United States Patent
Sheta et al.

(10) Patent No.: US 12,109,025 B2
(45) Date of Patent: Oct. 8, 2024

(54) SYSTEM AND METHOD FOR DETECTING A HEALTH CONDITION USING EYE IMAGES

(71) Applicant: AIZTECH CANADA INC., Vancouver (CA)

(72) Inventors: Mohamed Sheta, Vancouver (CA); Benjamin Fonooni, Vancouver (CA); Sara Leblanc, Vancouver (CA); Lingxiao Qi, Vancouver (CA)

(73) Assignee: AIZTECH CANADA INC., Vancouver (CA)

(*) Notice: Subject to any disclaimer, the term of this patent is extended or adjusted under 35 U.S.C. 154(b) by 0 days.

(21) Appl. No.: 18/205,296

(22) Filed: Jun. 2, 2023

(65) Prior Publication Data

US 2023/0346276 A1    Nov. 2, 2023

Related U.S. Application Data

(63) Continuation-in-part of application No. PCT/CA2021/051718, filed on Dec. 2, 2021.
(Continued)

(51) Int. Cl.
*A61B 5/16*    (2006.01)
*G06F 3/01*    (2006.01)
*G06V 40/18*    (2022.01)

(52) U.S. Cl.
CPC .............. *A61B 5/163* (2017.08); *G06F 3/013* (2013.01); *G06V 40/18* (2022.01)

(58) Field of Classification Search
CPC ......... A61B 5/163; A61B 3/113; A61B 3/117; A61B 3/1173; A61B 8/5238;
(Continued)

(56) References Cited

U.S. PATENT DOCUMENTS

2015/0116665 A1* 4/2015 Finkel ................... G16H 30/40
                                                               351/210
2017/0164830 A1    6/2017 Huang et al.
(Continued)

FOREIGN PATENT DOCUMENTS

IN    202041019896 A    5/2020

OTHER PUBLICATIONS

Extended European Search Report for corresponding Application No. 21899377.2-1122, dated Jul. 8, 2024, 6 pages.

*Primary Examiner* — Devin B Henson
*Assistant Examiner* — Matthew Eric Ogles
(74) *Attorney, Agent, or Firm* — Mintz, Levin, Cohn, Ferris, Glovsky and Popeo, P.C.

(57) ABSTRACT

Disclosed herein are systems, methods and devices for predicting whether a user has a target health condition using eye images. Automated guidance is provided to the user to obtain, using a computing device operated by the user, images including the user's sclera, each of the images corresponding to a guided direction of the user's gaze. Images are received from the computing device by way of a network. Images are subject to verification that sufficiently show the user's sclera, including by estimating a direction of the user's gaze and confirming that the estimated direction for a given one of the images conforms with the guided direction. Feature-enhanced image data are generated by applying an autoencoder to enhance features corresponding to the user's sclera in the images. A prediction of whether the user has the target health condition is generated by providing the feature-enhanced image data to a convolutional neural network.

18 Claims, 27 Drawing Sheets

Related U.S. Application Data

(60) Provisional application No. 63/277,372, filed on Nov. 9, 2021, provisional application No. 63/121,683, filed on Dec. 4, 2020.

(58) Field of Classification Search
CPC ............... A61B 8/5269; A61B 8/5292; A61B 5/1128; A61B 5/1176; A61B 6/563; A61B 2090/364; A61B 5/0013; A61B 5/004; A61B 5/0017; A61B 8/5207; A61B 3/1216; A61B 3/14; A61B 3/145; G06F 3/013; G06F 3/017; G06V 40/18; G06V 40/179; G06V 40/20; G06V 40/382; G06V 40/394; G06V 40/50; G06V 40/70; G06V 2201/03

See application file for complete search history.

(56) References Cited

U.S. PATENT DOCUMENTS

| | | |
|---|---|---|
| 2017/0189230 A1* | 7/2017 | Fateh ................... H04N 9/3173 |
| 2018/0125404 A1* | 5/2018 | Bott ....................... H04N 23/64 |
| 2019/0038129 A1 | 2/2019 | Ong et al. |
| 2020/0337554 A1 | 10/2020 | Shin et al. |
| 2021/0034836 A1* | 2/2021 | Haimovitch-Yogev ...................... G06N 3/04 |
| 2022/0084197 A1* | 3/2022 | Wyder ................... G06V 10/26 |
| 2022/0165421 A1* | 5/2022 | Lewis ................... G06T 7/0012 |

\* cited by examiner

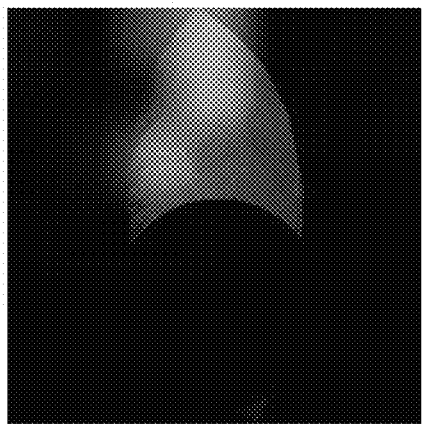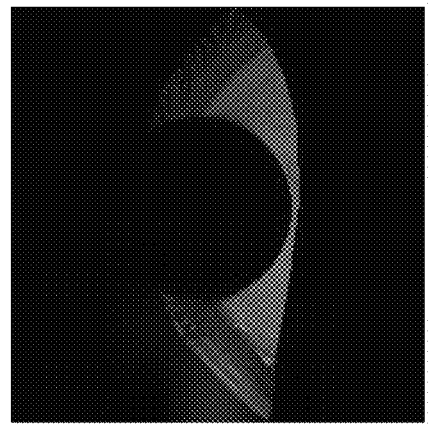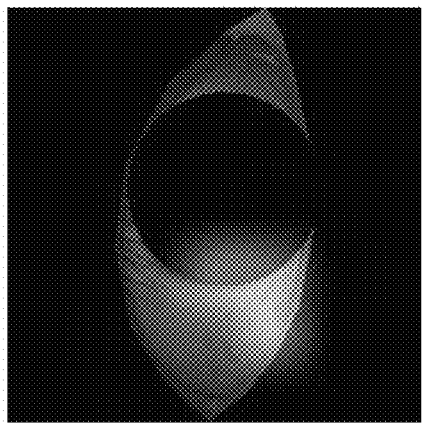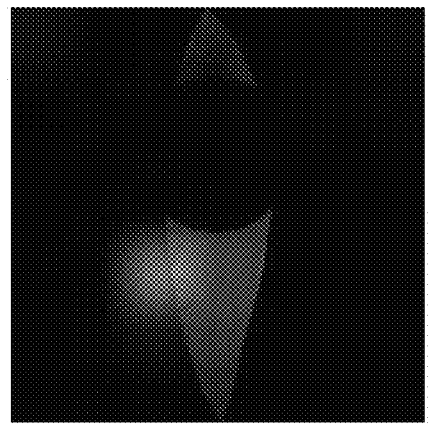
FIG. 16A

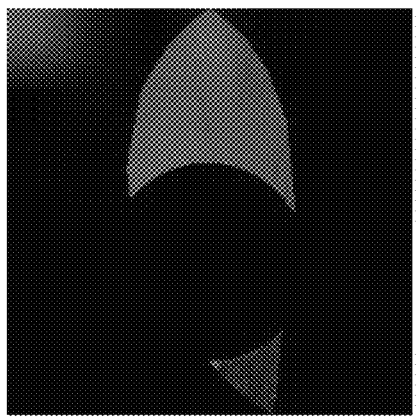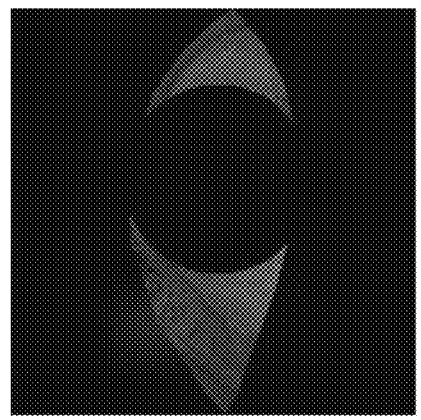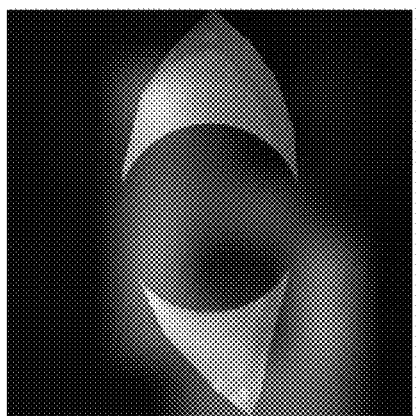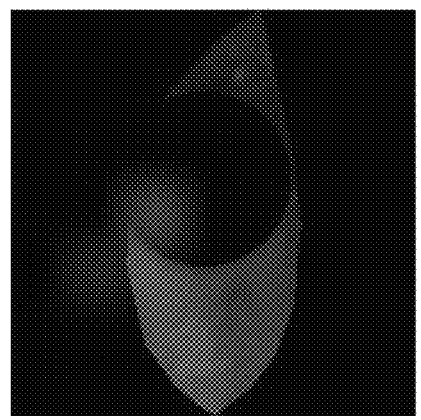
FIG. 16B

SYSTEM AND METHOD FOR DETECTING A HEALTH CONDITION USING EYE IMAGES

CROSS-REFERENCE TO RELATED APPLICATIONS

This application is a continuation-in-part of PCT patent application no. PCT/CA2021/051718 filed Dec. 2, 2021, which claims all benefit including priority to U.S. Provisional Patent Application 63/121,683, filed Dec. 4, 2020 and U.S. Provisional Patent Application 63/277,372, filed Nov. 9, 2021, the entire contents of all of which are hereby incorporated by reference herein.

FIELD

This disclosure relates generally to machine learning, and more specifically to using deep machine learning for detecting a health condition using eye images.

BACKGROUND

Coronavirus disease (COVID-19) is an infectious disease caused by the SARS-CoV-2 virus. The COVID-19 pandemic has devastated the population impacting millions of people worldwide. The standard method of testing patients for infection by the SARS-CoV-2 virus involves reverse transcription polymerase chain reaction (RT-PCR) tests, antigen tests, antibody tests and computed tomography (CT) imaging. However, these methods are expensive, involve professional intervention and a prolonged amount of waiting time to receive the results. Accordingly, there is a need for improved methods for COVID-19 testing.

SUMMARY

In accordance with an aspect, there is provided a computer-implemented method for predicting whether a user has a target health condition using eye images. The method includes: providing automated guidance to the user to obtain, using a computing device operated by the user, a plurality of images including the user's sclera, each of the images corresponding to a guided direction of the user's gaze; receiving the images from the computing device by way of a network; verifying that the images sufficiently show the user's sclera, including by estimating a direction of the user's gaze and confirming that the estimated direction for a given one of the images conforms with the guided direction corresponding to that image; generating feature-enhanced image data by applying an autoencoder to enhance features corresponding to the user's sclera in the images; and computing a prediction of whether the user has the target health condition by providing the feature-enhanced image data to a convolutional neural network.

In some embodiments, the target health condition is a disease caused by a coronavirus, such as, for example, COVID-19.

In some embodiments, the automated guidance provides voice guidance to the user.

In some embodiments, the automated guidance provides the voice guidance in real time based on the direction of the user's gaze.

In some embodiments, the plurality of images include four images corresponding to the user's gaze being in the up, down, left, and right directions.

In some embodiments, the features include features of ocular manifestations associated with the target health condition.

In some embodiments, the convolutional neural network includes at least 16 layers.

In some embodiments, the autoencoder comprises a convolutional neural network.

In some embodiments, the method may further include: transmitting to the computing device operated by the user an indication of whether the user has the target health condition based on the prediction.

In some embodiments, at least one image from the plurality of images contains a face of the user, and generating feature-enhanced image data of the at least one image comprises detecting the face of the user and extracting an eye of the user from the detected face of the user.

In some embodiments, generating feature-enhanced image data further comprises masking an iris area of the eye of the user in the at least one image.

In accordance with another aspect, there is provided a computer-implemented system for predicting whether a user has a target health condition using eye images. The system includes at least one processor; memory in communication with the at least one processor, and software code stored in the memory. The software code, when executed by the at least one processor causes the system to: provide automated guidance to the user to obtain, using a computing device operated by the user, a plurality of images including the user's sclera, each of the images corresponding to a guided direction of the user's gaze; receive the images from the computing device by way of a network; verify that the images sufficiently show the user's sclera, including by estimating a direction of the user's gaze and confirming that the estimated direction for a given one of the images conforms with the guided direction corresponding to that image; generate feature-enhanced image data by applying an autoencoder to enhance features corresponding to the user's sclera in the images; and compute a prediction of whether the user has the target health condition by providing the feature-enhanced image data to a convolutional neural network.

In some embodiments, the target health condition is a disease caused by a coronavirus, such as, for example, COVID-19.

In some embodiments, the automated guidance provides voice guidance to the user.

In some embodiments, the automated guidance provides the voice guidance in real time based on the direction of the user's gaze.

In some embodiments, the plurality of images include four images corresponding to the user's gaze being in the up, down, left, and right directions.

In some embodiments, the features include features of ocular manifestations associated with the target health condition.

In some embodiments, the convolutional neural network includes at least 16 layers.

In some embodiments, the autoencoder comprises a convolutional neural network.

In some embodiments, the system may further be configured to: transmitting to the computing device operated by the user an indication of whether the user has the target health condition based on the prediction.

In some embodiments, at least one image from the plurality of images contains a face of the user, and generating feature-enhanced image data of the at least one image comprises detecting the face of the user and extracting an eye of the user from the detected face of the user.

In some embodiments, generating feature-enhanced image data further comprises masking an iris area of the eye of the user in the at least one image.

In accordance with a further aspect, there is provided a non-transitory computer-readable medium having stored thereon machine interpretable instructions which, when executed by a processor, cause the processor to perform the foregoing methods.

Many further features and combinations thereof concerning embodiments described herein will appear to those skilled in the art following a reading of the instant disclosure.

BRIEF DESCRIPTION OF THE DRAWINGS

In the Figures,

FIG. 16A illustrates the Grad-CAM maps for eye images that were predicted as COVID-19 positive;

FIG. 16B illustrates the Grad-CAM maps for eye images predicted as COVID-19 negative;

These drawings depict exemplary embodiments for illustrative purposes, and variations, alternative configurations, alternative components and modifications may be made to these exemplary embodiments.

DETAILED DESCRIPTION

Figure 1:
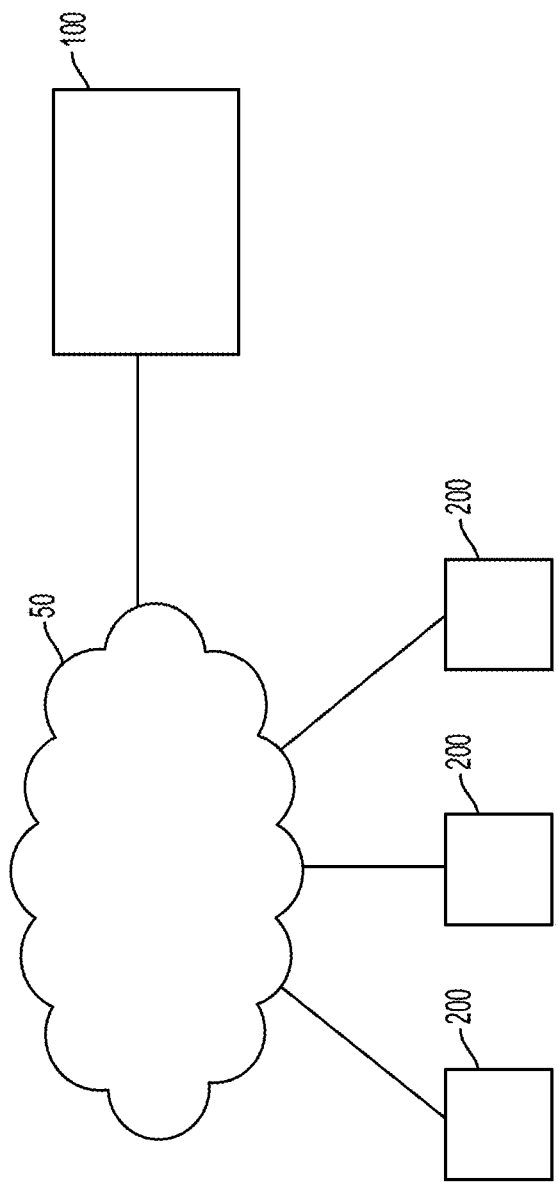
FIG. 1 is a network diagram of a network environment of an example system for remote assessment of a target health condition, in accordance with an embodiment.

FIG. 1 is a diagram depicting a network environment for remote assessment of whether a user has a particular health condition (e.g., COVID-19) based on processing images of the user's eye, in accordance with an embodiment. As depicted, the network environment includes an assessment system 100 interconnected with a plurality of end user devices 200 by way of a communication network 50.

In the depicted embodiment, assessment system 100 detects whether a user has COVID-19 upon assessment of whether a user's eye shows symptoms of COVID-19. Assessment system 100 be used, for example, to test and screen users for COVID-19. In other embodiments, as detailed herein, assessment system 100 may be adapted to assess whether a user has another health condition that is the target of testing or screening, which may be referred to as a target health condition.

As detailed herein, various embodiments of assessment system 100 performs detection by applying deep machine learning to data defining eye images. The assessment includes processing such data to detect the presence of features corresponding to ocular manifestations of COVID-19. In accordance with this assessment, assessment system 100 generates a prediction of whether a particular end user has COVID-19 (e.g., is infected with the SARS-CoV-2 virus).

Ocular manifestations of COVID-19 have been observed. The receptors involved in COVID-19 infection of the cell, namely ACE2, CD147, CTSL and TMPRSS2 are found in both ocular and non-ocular parts of the body that have been recognized in the literature as targets for the COVID-19 infection. In ocular cells, ACE2 and TMPRSS2 have shown the highest expression in goblet cells when compared with other cell types in the conjunctiva including Epithelial cells, Endothelial cells and Fibroblasts to name a few.

Once COVID-19 penetrates an ocular cell, changes happen on a cellular, ocular surface and retinal level. The prevalence of ocular surface, eyelid and anterior segment manifestations has ranged from 0.81% to 34.5% across studies, e.g, as shown in Sen, S., Kannan, N. B., Kumar, J., Rajan, R. P., Kumar, K., Baliga, G., . . . & Ramasamy, K. (2021a. Retinal manifestations in patients with SARS-CoV-2 infection and pathogenetic implications: a systematic review. International Ophthalmology, 1-14). In ICU patients, the incidence of COVID-19 eye related complications has varied from 3% to 60% across studies (Bertoli, F., Veritti, D., Danese, C., Samassa, F., Sarao, V., Rassu, N., . . . & Lanzetta, P. (2020). Ocular findings in COVID-19 patients: a review of direct manifestations and indirect effects on the eye. Journal of ophthalmology, 2020). At the cellular level, goblet cells show a decreased density and cell size. In the non-goblet cells due to COVID-19, squamous changes, moderate to high enlargement and increased nucleocytoplasmic ratio occur (Bozkurt, E., Özateş, S., Muhafiz, E., Yilmaz, F., & Caliskan, O. (2020). Ocular Surface and Conjunctival Cytology Findings in Patients with Confirmed COVID-19. Eye & Contact Lens, 2020). In addition, epithelial cells appear polygonal in shape in patients with COVID-19. These pathological ocular surface changes can be present at the early stages of the infection even in the absence of clinically significant ocular manifestation.

Various embodiments of assessment system 100 may provide one or more of the following conveniences: the COVID-19 assessment can be performed rapidly (e.g., with results provided in minutes), remotely (e.g., with the end user at home), non-invasively (e.g., without the need to obtain any physical sample), on demand by the user at any time, and without intervention by a medical professional.

Various embodiments of assessment system 100 may be applied to one or more of the following uses:

Rapid, non-invasive screening of infected individuals at the early stages of the COVID-19 infection since ocular manifestations may appear 7-10 days before pulmonary symptoms.

Help containment strategy of viral transmission by alerting infected individuals to self-quarantine by detecting an eye symptom, which is the first presenting symptom of infection in some cases Surveillance testing of mass populations using a non-invasive. real-time, highly scalable technology solution that is easily deployable to security cameras at checkpoints, e.g., airports, schools, shopping malls, or the like.

Guide public health policies based on aggregation of rapid testing results across a population.

Accelerate return to a back-to-normal lifestyle and minimizes the need to shut down the economy by connecting individuals to rapid, on-demand testing results and predicting infection load and infection risk at the office or other locations to facilitate day-to-day decision-making.

Continuing to refer to FIG. 1, in an aspect, assessment system 100 provides a web application that allows a plurality of end users to provide images for assessment and to obtain assessment results. An end user may access assessment system 100 by operating an end user device 200 (which may be referred to as a device 200 for convenience).

A device 200 is operable by an end user to access a web application provided by assessment system 100. A device 200 includes one or more cameras operable by the end user to capture images of him/herself including his/her eyes. In some embodiments, device 200 is operable by an end user to obtain an image without assistance from any other person, e.g., to obtain a "selfie" image.

A device 200 may, for example, be a smartphone, a tablet, a laptop device, or the like, having an integrated camera. A device 200 may also be, for example, another computing device such as a desktop computer having an external camera such as a webcam. In either case, the camera is capable of capturing images having a sufficient resolution for processing by assessment system 100 in manners described herein. In the depicted embodiment, an image resolution of 1920 pixels by 1080 pixels is sufficient. The minimum required image resolution may depend on various factors, including for example, the intended use case, the desired level of accuracy, and the particular condition(s) under assessment, and other factors.

Network 50 may include a packet-switched network portion, a circuit-switched network portion, or a combination thereof. Network 50 may include wired links, wireless links such as radio-frequency links or satellite links, or a combination thereof. Network 50 may include wired access points and wireless access points. Portions of network 50 could be, for example, an IPv4, IPv6, X.25, IPX or similar network. Portions of network 50 could be, for example, a GSM, GPRS, 3G, LTE or similar wireless networks. Network 50 may include or be connected to the Internet. When network 50 is a public network such as the public Internet, it may be secured as a virtual private network.

Figure 2:
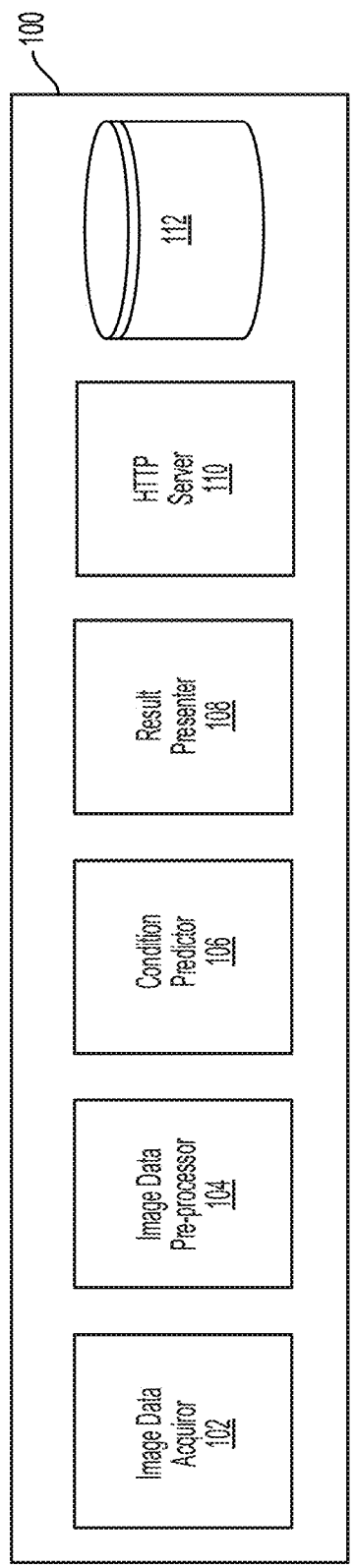
FIG. 2 is a schematic diagram of the system of FIG. 1, in accordance with an embodiment.

FIG. 2 is a high-level schematic of assessment system 100, in accordance with an embodiment. As depicted, assessment system 100 includes an image data acquirer 102, an image data pre-processor 104, a condition predictor 106, a result presenter 108, an HTTP server 110, and an electronic data store 112.

Image data acquirer 102 is configured to obtain, from the end user, image data required for assessment, i.e., for processing of the image data and applying deep machine learning to predict whether a particular end user has COVID-19.

Image data acquirer 102 is configured to cooperate with HTTP server 110 to obtain image data from the end user. For example, image data acquirer 102 may cause HTTP server 110 to provide a web application that obtains image data using a camera at the device 200 operated by the end user. For another example, image data acquirer 102 may receive image data from an external mobile application that obtains image data using a camera at a mobile device 200 operated by the end user. The image data may be transmitted wirelessly from the mobile device 200.

In some embodiments, the image data acquired by image data acquirer 102 may include one or more images of one or more eyes, such as one or more images of a left eye, and/or one or more images of a right eye, of the user.

In some embodiments, the image data acquired by image data acquirer 102 may include one or more images of a face of the user. When the image data includes one or more images of a face of the user, a face recognition technique may be implemented to locate the face and more specifically, left and right eyes in each image of the face. For example, the face recognition technique may be implemented as part of an eye data extractor 142, further elaborated below.

Figure 3:
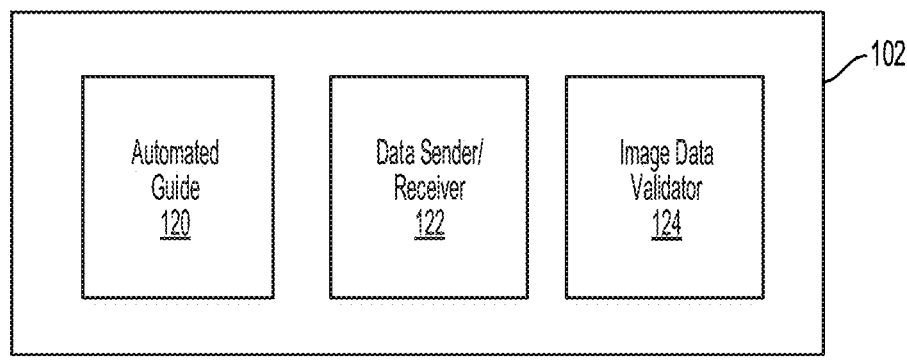
FIG. 3 is a schematic diagram of an image data acquirer of the system of FIG. 1, in accordance with an embodiment.

Referring to FIG. 3, in the depicted embodiment, image data acquirer 102 includes an automated guide 120, a data sender/receiver 122, and an image data validator 124.

Automated guide 120 is configured to provide computer-generated guidance to guide an end user through an image acquisition process for capturing images needed by assessment system 100. In the depicted embodiment, automated guide 120 guides an end user to capture a set of four images corresponding to a user's gaze in each of the center, left, right, and up directions. In the depicted embodiment, automated guide 120 provides voice guidance that provides verbal instructions to the end user. The verbal instructions may include, for example, pre-recorded speech segments and/or computer-generated speech.

In some embodiments, automated guide 120 may request that the user provide consent to the assessment prior to any images being obtained.

Data sender/receiver 122 is configured to cause image data reflecting the set of images captured at device 200 to be sent to assessment system 100. A portion of data sender/receiver 122 may be included as part the a web application provided by assessment system 100 to device 200 and executed at device 200, where it causes the data to be sent from device 200 to assessment system 100. A portion of data send/receiver 122 may be executed at assessment system 100.

Data sender/receiver 122 may cause the image data to be sent through a secure channel, e.g., using one or more known encryption/decryption processes. Data sender/receiver 122 may cause the image data to be sent via a REST API. Data sender/receiver 122 may cause the image data to be sent in a known encoding format such as PNG, JPEG, TIFF, or the like, where it can be decoded at assessment system 100 to provide an array of pixel values (e.g., RGB values. In some embodiments, data sender/receiver 122 may cause image data to be resized and/or compressed at device 200 to facilitate efficient data transmission to assessment system 100.

Image data validator 124 processes image data received at assessment system 100 from device 200, to validate that the data meet requirements for downstream processing. For example, image data validator 124 verifies that the image data sufficiently show the user's sclera.

Figure 4A:
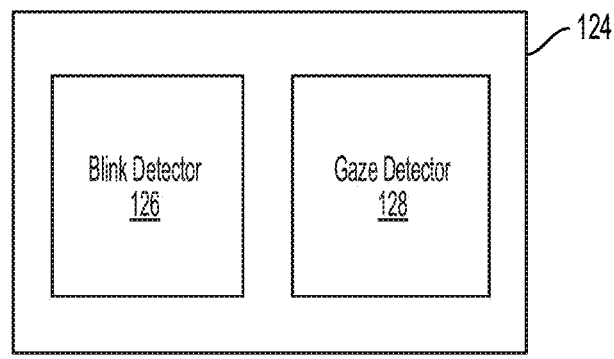
FIG. 4A is a schematic diagram of an image data validator of the image data acquirer of FIG. 3, in accordance with an embodiment.

Referring to FIG. 4A, in the depicted embodiment, image data validator 124 includes a blink detector 126 and a gaze detector 128.

Blink detector 126 is configured to process image data for an image of the user, and provide an indication of whether or not the user's eye is closed (e.g., due to a blink). Image data validator 124 is configured to signal an error condition when blink detector 126 indicates that the user's eye is closed.

Gaze detector 128 is configured to process image data for an image of the user, and provide an estimate of the direction of the user's gaze, e.g., whether the user is looking in an expected one of the center, left, right, and up directions as requested by automated guide 120. Image data validator 124 is configured to signal an error condition when the user is not looking in an expected direction in one or more of the images.

In some embodiments, when the input image includes a face of the user, image data validator 124 may execute a face recognition model to locate the face in the image and based on the coordinates of the iris, eye corners, and eyelids, verifies the user's gaze directions as requested by automated guide 120. In some embodiments, when there are more than one images, such as four images, each with a different gaze direction, the four images are all verified by the face recognition model of the image data validator 124 prior to extracting any eye image by downstream processing (e.g., such as by eye image extractor 142).

Figure 4B:
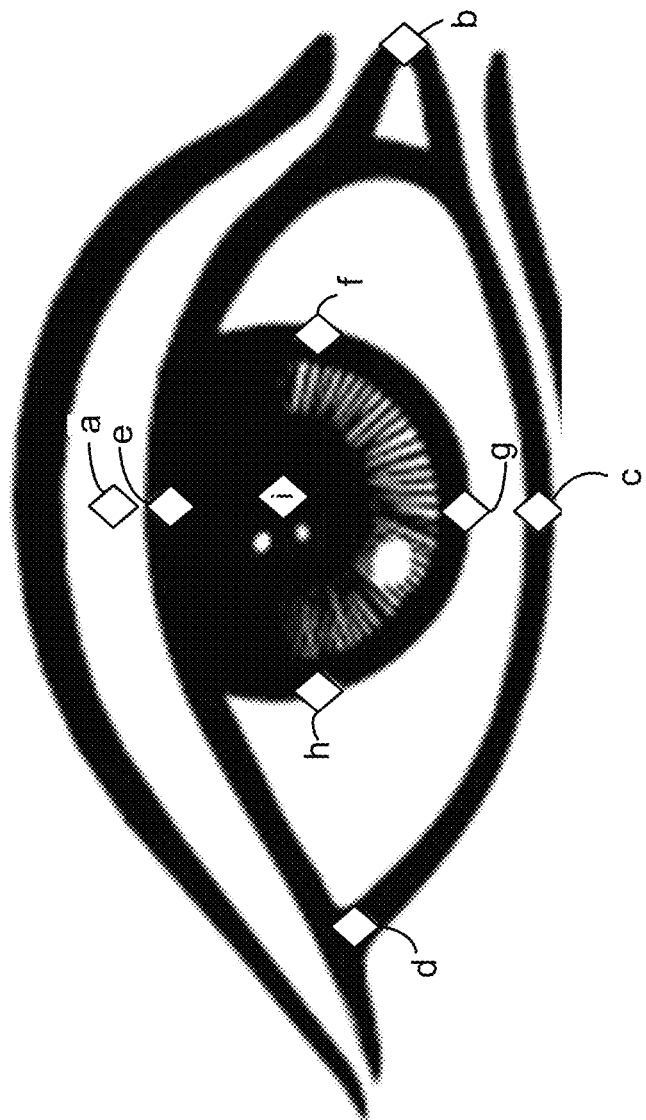
FIG. 4B is an example eye with various landmarks used to determine a gaze or a blink, in accordance with an embodiments.

FIG. 4B shows an example schematic diagram of an eye with various landmarks for determining a user's gaze. Let D be the Euclidean distance function on a 2D plane such that D(point1, point2) is the Euclidean distance between point1 and point2. In order to detect if a user's gaze is centered, the Euclidean distances D(d, i), D(b, i) and D(d, b) are calculated, then the difference between D(d, i) and D(b, i) is calculated according to the equation below:

$$\text{diff} = \text{abs}(D(d,i) - D(b,i)),$$

where abs( ) is the absolute function.

Next, the difference diff=abs(D(d, i)−D(b, i)) is normalized to obtain a ratio based on D(d, b): ratio=diff/D(d, b). If both eyes' respective ratios are smaller than a threshold (e.g., 0.29), the user's gaze can be considered to be centered.

If the user's eyes are not centered and for both eyes D(b,i)<D(d,i), the user's gaze is considered to point to the right. If the user's eyes are not centered and for both eyes D(b,i)>D(d,i), the user's gaze is considered to point to the left.

To detect if the user is looking up, the y coordinates of the points, as represented by point.y can be used to calculate:

$$\text{vertical diff} = c \cdot y - g \cdot y;$$

$$\text{height} = c \cdot y - a \cdot y;$$

and $$\text{vertical ratio} = \text{vertical diff/height}.$$

If the vertical ratio is greater than 0.05, the user's gaze is considered to point up.

In order to detect a blink, again referring to FIG. 4B, D(a, c) and D(d, b) can be used to determine a blink ratio in accordance with the following equation:

$$\text{blink ratio} = D(d,b)/D(a,c)$$

If the average blink ratio of the two eyes is greater than 3.8, the user is considered to be blinking.

In some embodiments, image data validator 124 may be configured to process image data reflecting a user's set of images and confirm that each image in the set show the same individual. Image data validator 124 may be configured to signal an error condition when not all images in the set show the same individual In some embodiments, image data validator 124 may be configured to process image data reflecting a user's set of images, and confirm, for each image in the set, that the user is located an appropriate distance from the camera. For example, an appropriate distance is one at which the distance is near enough such that the image portion of an eye is sufficiently large for downstream processing, but far enough to capture substantially all of the user's eyes. Image data validator 124 may be configured to signal an error condition when the user is not located at an appropriate distance.

In some embodiments, image data validator 124 may be configured to process image data reflecting a user's set of images, and confirm, for each image in the set, that the user's eyes are sufficiently lit. Image data validator 124 may be configured to signal an error condition when the user's eyes are not sufficiently lit.

In the depicted embodiment, image data validator 124 resides at assessment system 100 and is executed at assessment system 100. In some embodiments, some or all of image data validator 124 may be provided by assessment system 100 to device 200 as part of the aforementioned web application and be executed at device 200.

Automated guide 120 and image data validator 124 are configured to operate in concert such that automated user assistant 120 provides guidance based on the validation results computed by image data validator 124. For example, when image data validator 124 signals an error condition, automated guide 120 may request that user re-capture one or more of the required images.

In some embodiments, automated guidance 120 may provide guidance in real time (or near real time) so that guidance is provided promptly to the user (which collectively may be referred to as "real time" for convenience). For example, upon detecting that user is looking in an unexpected direction (e.g., by operation of gaze detector 128), automated guide 120 may provide voice guidance instructing the user to look in the expected direction. In other examples, other types of instructions may be provided, e.g., to move the camera closer or farther from the user's face, to improve lighting, etc.

In some embodiments, image data acquirer 102 is configured to receive a video stream of the end user as the end user follows a guidance system. Image data acquirer 102 then extracts the required images (e.g., with the end user having a gaze direction that is centre, left, right, up, etc.) automatically from the video stream. Image data acquirer 102 may evaluate the video stream data to identify the most suitable images (e.g., with the least motion blur, without blinking, with an expected gaze direction, etc.)

Figure 5:
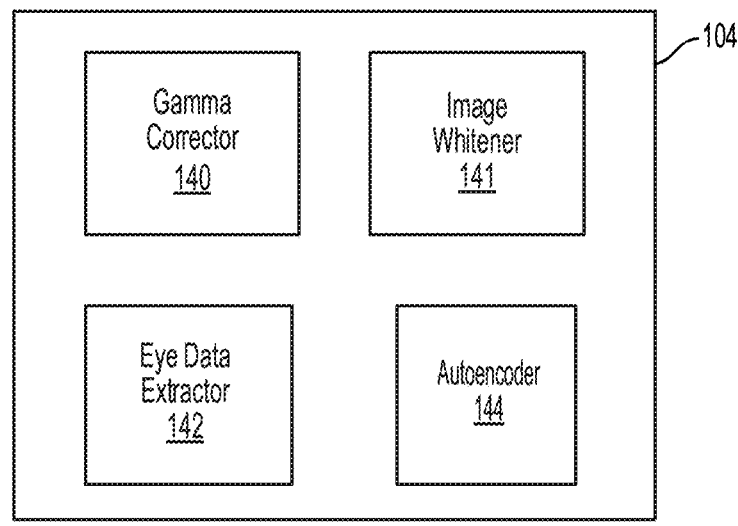
FIG. 5 is a schematic diagram of an image data preprocessor of the system of FIG. 1, in accordance with an embodiment.

Image data pre-processor 104 is configured to apply pre-processing to image data to facilitate downstream processing. Referring to FIG. 5, in the depicted embodiment, image data pre-processor 104 includes a gamma corrector 140, image whitener 141, an eye data extractor 142, and an autoencoder 144.

Gamma corrector 140 is configured to process image data for an image of the user and, if required, apply gamma correction to adjust the brightness of the image.

Image whitener 141 is configured to process image data for an image of the user and, if required, apply an appropriate amount of image whitening to adjust the color temperature of the image.

Eye data extractor 142 is configured to process image data for an image of the user to extract regions of the image (e.g., a subset of pixels) containing one or both eyes. For example, for each image, eye data extractor 142 may generate two image portions, each containing a respective image region with one of the user's left and right eyes. In some embodiments, a face recognition model, which may be implemented as a standalone model, or implemented as part of image data validator 124 or eye data extractor 142, locates the face in the image of the user. Once the face is recognized, image data validator 124 may, based on the coordinates of the iris, eye corners, and eyelids, crop the respective eye image of each eye, based on the eye coordinates. In some embodiments, prior to extracting the eye images by eye data extractor 142, image data validator 124 first verifies the user's gaze directions in the image, as elaborated above.

Eye data extractor 142 applies a mask to the image portions such that non-eye pixels are set to a value of 0. In the depicted embodiment, eye data extractor 142 implements a Haar-based algorithm to detect the face and then to detect the location of each eye.

Autoencoder 144 is configured to process image data reflecting an eye region (e.g., as provided by eye data extractor 142) to enhance relevant features e.g., features corresponding to ocular manifestations of a target health condition. In the depicted embodiment, autoencoder 144 is configured to enhance features corresponding to the user's sclera including ocular manifestations in and around the sclera. Pre-processing image data using autoencoder 144 helps the deep learning neural network focus on relevant features in the image data.

In the depicted embodiment, autoencoder 144 receives image data of an eye including 296×296 pixels of RGB data, and may produce an output of 74×74 pixels of RGB data. In this way, the quantity of data is also reduced for downstream processing.

In the depicted embodiment, autoencoder 144 is implemented as a convolutional neural network (distinct from neural network 160). The neural network includes an input layer, a plurality of hidden layers, and an output layer. The hidden layers may be implemented using a combination of 2D convolutional layers and pooling layers (which may be max-pooling layers). The layers may be implemented using a suitable combinations of filters and kernels, and activation functions such as, e.g., Rectified Linear Unit (ReLU) activation.

The output of image data pre-processor, i.e., pre-processed data including an array or matrix of autoencoder-generated features, is provided to condition predictor 106.

Condition predictor 106 is configured to process the pre-processed to generate a prediction of whether the user has the target health condition, i.e., COVID-19 or otherwise.

Figure 6:
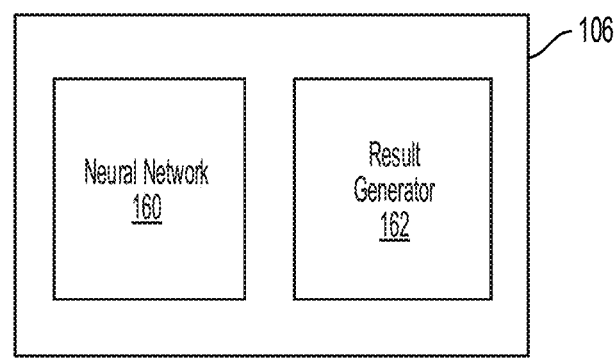
FIG. 6 is a schematic diagram of a condition predictor of the system of FIG. 1, in accordance with an embodiment.

Referring to FIG. 6, in the depicted embodiment, condition predictor 106 includes a neural network 160 and a result generator 162.

Neural network 160 implements a deep learning model trained to detect ocular manifestations that indicate the user has symptoms of COVID-19. In particular, neural network 160 receives as an input autoencoder-generated feature data corresponding to an image region of a single eye of a user. Neural network 160 generates as an output a probability metric of an eye indicating that the user has COVID-19. This may be repeated for each eye in the set of images provided by the user. For example, given a set of four images and two eyes per image, neural network 160 may generate eight separate probability metrics. These probability metrics are provided to result generator 162.

Figure 7:
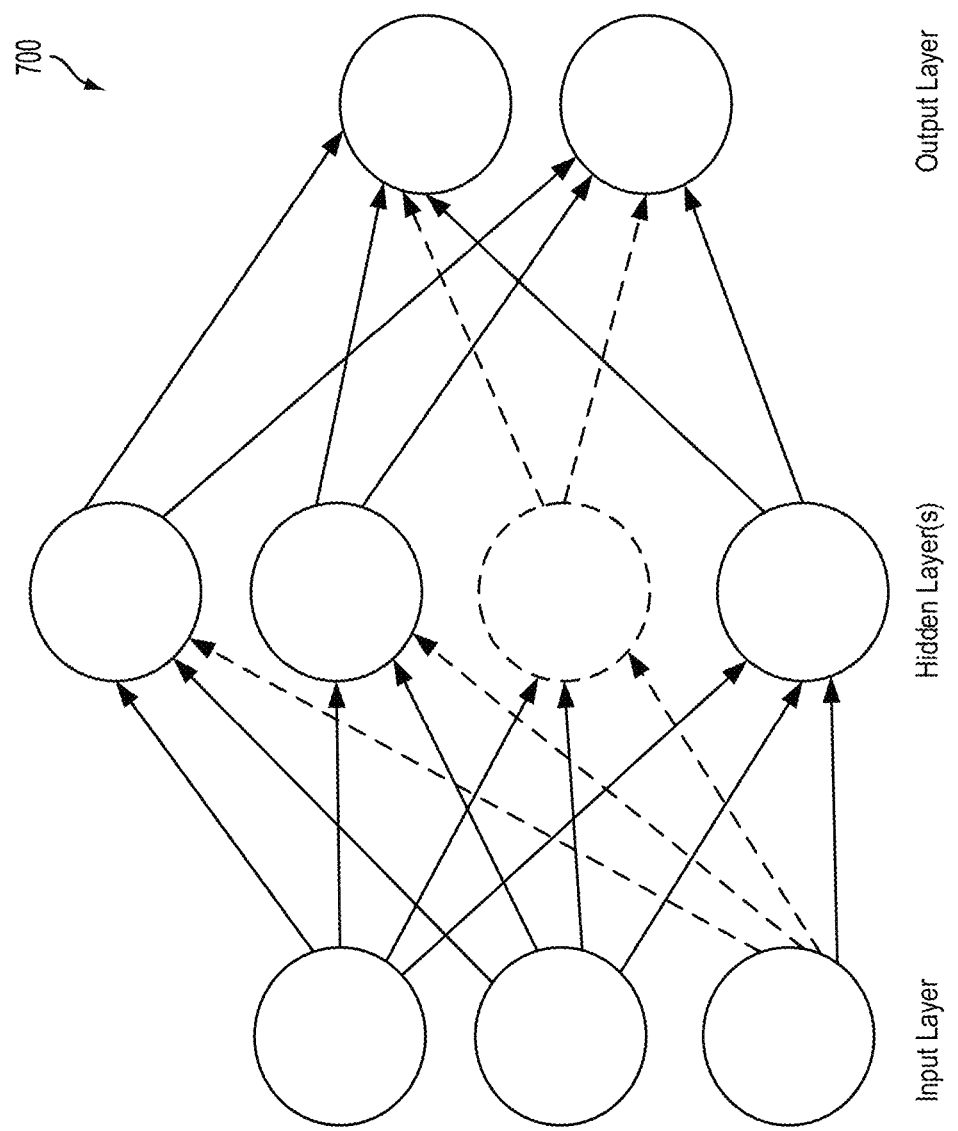
FIG. 7 is a schematic diagram of an example architecture of a neural network of the condition predictor of FIG. 6, in accordance with an embodiment.

As depicted in FIG. 7, neural network 160 may have an architecture 700 including an input layer, a plurality of hidden layers, and an output layer. The input layer receives the auto-encoder generated features. The hidden layers map the input layer to the output layer. The output layer provides the prediction of neural network 160. In the depicted embodiment, neural network is a convolutional neural network. In other embodiments, other suitable deep learning models and architectures can be used.

Figure 8A:
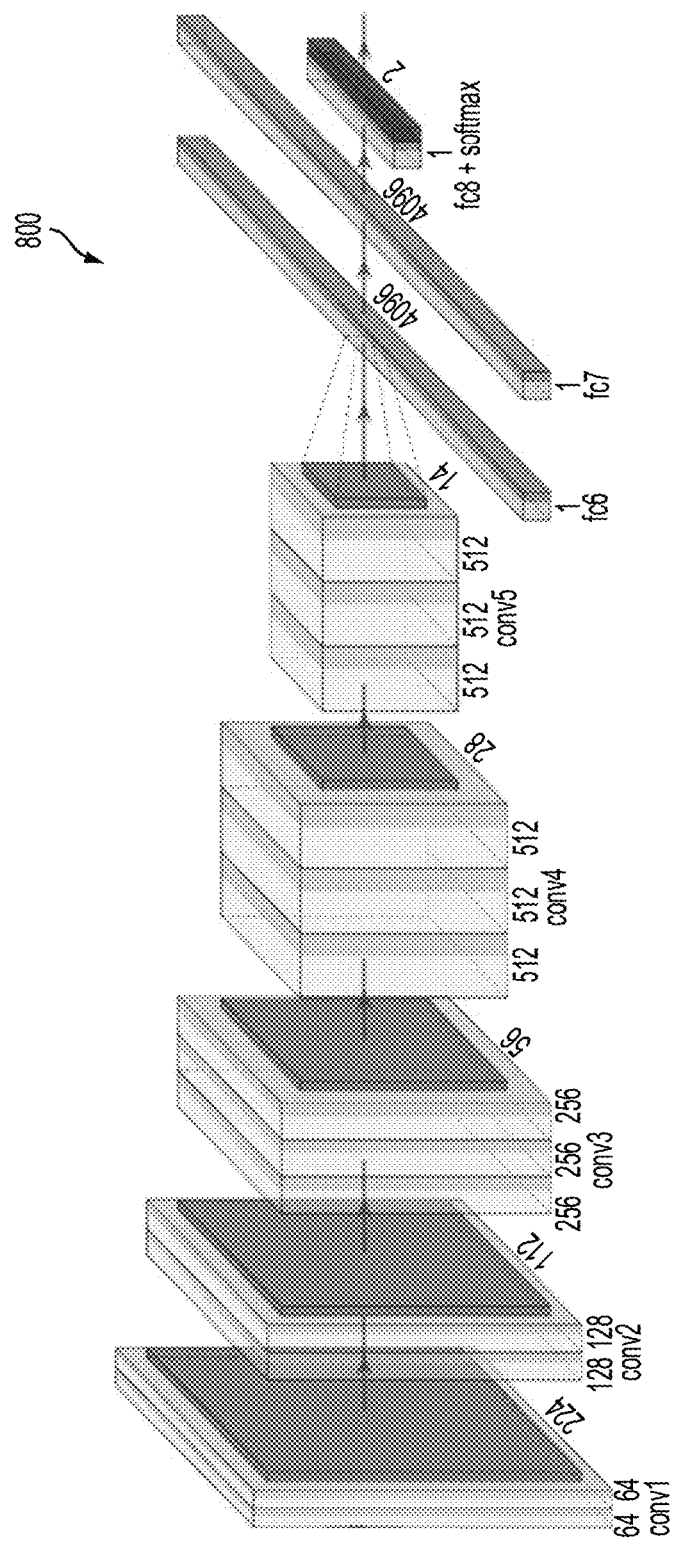
FIG. 8A is a schematic diagram of a more detailed example architecture of a neural network of the condition predictor of FIG. 6, in accordance with an embodiment.

FIG. 8A depicts in greater detail an example implementation of neural network 160, in accordance with an embodiment. As depicted, in this embodiment, neural network 160 implements a convolutional neural network having a VGG16 architecture 800 (K Simonyan, A Zisserman (2014) Very deep convolutional networks for large-scale image recognition, arXiv preprint arXiv:1409.1556) with a Softmax as an output layer to predict the probability of having COVID-19. The Softmax layer is configured with two classes where the outputs are probabilities of the patient having COVID-19 and the patient being healthy or having other ocular diseases (non-COVID-19).

As shown in FIG. 8A, the convolutional layers use a receptive field of 3×3; the convolution stride is set to 1 pixel such that the spatial resolution is preserved after convolution; spatial pooling is performed by five max-pooling layers; three fully connected layers are added after the convolutional layers where the first two have 4096 channels and the third one has 2 channels that corresponds to the number of classes that the model is able to classify. As noted, the last layer is a Softmax layer where the prediction for each of the classes (COVID-19 or non-COVID-19) is determined.

In other embodiments, neural network 160 may use another suitable deep learning model and/or implement another suitable deep learning architecture. In such embodiments, the number and types of layers may vary. In particular, in some embodiments, the number of layers may be more than shown in FIG. 8A. For example, in some embodiments, neural network 160 includes at least 30 layers. For example, in some embodiments, neural network 160 includes at least 50 layers. The layers may include a suitable combination of convolutional layers, ReLU activation layers, and max-pooling layers. In some embodiments, the layers may also include batch normalization layers, dropout layers, dense layers, flattening layers, and other types of pooling layers, and the like. In some embodiments, neural network 160 may be a type of neural network other than a convolutional neural network.

Figure 8B:
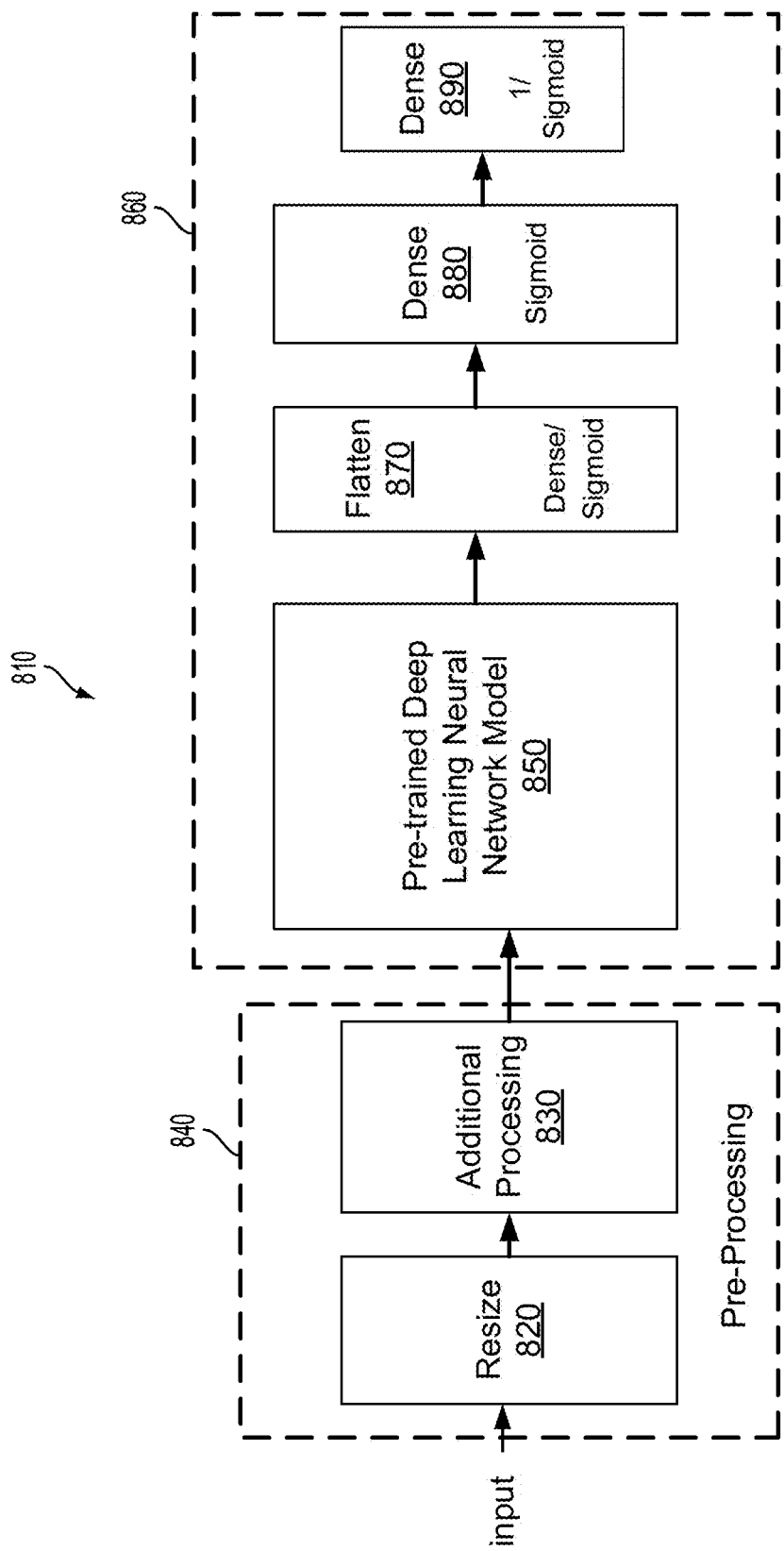
FIG. 8B is a schematic diagram of another example architecture of a neural network of the condition predictor of FIG. 6, in accordance with an embodiment.

FIG. 8B shows a schematic diagram of another example architecture 810 of a neural network 860, which can be implemented as an embodiment of the neural network 160 of the condition predictor of FIG. 6. The input image may be first pre-processed by a pre-processor model 840, which may include, for example, similar functionalities of image data pre-processor 104. The pre-processing performed by pre-processor model 840 may include a resizing step 820 and additional processing 830. The additional processing 830 may include, for example, actions performed by gamma corrector 140 and image whitener 141 of image data pre-processor 104.

In some embodiments, pre-processor model 840 may include a filtration process, during which input images that can result in false positives or false negatives may be rejected. In the case of rejection, a message displaying one or more potential correction steps may be shown to the user at a user interface.

Neural network model 860 is pre-trained to receive input images having all eye-directions. In some embodiments, neural network model 860 may be trained with masked iris images, and may include a pre-trained deep learning model 850 that acts as a feature extractor. In some embodiments, the final three output layers 870, 880, 890 of the neural network model 860, which may include flattening, dense and sigmoid layers, are trained on the masked iris images from pre-trained deep learning model 850.

In some embodiments, pre-trained deep learning model 850 is trained on the ImageNet dataset, and the input image may be resized and pre-processed by pre-processing model 840 as necessary. Pre-trained deep learning model 850 is configured to generate features that are masked regions of the eye image, e.g., an iris region.

In some embodiments, pre-trained deep learning model 850 is configured to process image data for an image of the user to extract regions of the image (e.g., a subset of pixels) containing one or both eyes. In some embodiments, a face recognition model, which may be implemented as a stand-alone model, or implemented as part of pre-trained deep learning model 850 or eye data extractor 142, locates pixels belonging to a face of the user in the image of the user. Once the face is recognized, image data validator 124 may, based on the coordinates of the iris, eye corners, and eyelids, crop the respective eye image of each eye, based on the eye coordinates. In some embodiments, prior to extracting the eye images by eye data extractor 142, image data validator 124 first verifies the user's gaze directions in the image, as elaborated above.

In some embodiments, as an example, pre-trained deep learning model 850, or eye extractor, may implement Google's open source MediaPipe Solutions to first detect a human face in the input image and then extract the pixels belonging to the eyes in the extracted face. MediaPipe is a face geometry solution that estimates 478 3D face landmarks in real-time, even on mobile devices. It employs Machine Learning (ML) to infer the 3D surface geometry, requiring only a single camera input without the need for a dedicated depth sensor. Utilizing lightweight model architectures together with GPU acceleration throughout the pipeline, the solution delivers real-time performance critical for live experiences. MediaPipe also provides iris landmarks based on an ML solution for accurate iris estimation, able to track ocular landmarks involving the iris, pupil and the eye contours using a single RGB camera, in real-time, without the need for specialized hardware. Accurately tracking the iris within an eye is a challenging task to solve on mobile devices, due to the limited computational resources, variable light conditions and the presence of occlusions, such as hair or people squinting. The iris and face landmarks provide key information to obtain pixels of the eye(s), and mask the iris and skin area of the eye accordingly.

After training and testing a number of machine learning models, very high accuracy was observed on some datasets but poor overall performance was observed on the test sets. After further investigations, it was discovered that the machine learning models were affected by distinct reflection patterns between positive and negative classes, mainly as a result of the iris area in the eyes. It was concluded that the machine learning models that performed poor on some test sets was doing classification partly based on the reflections the eyes, which is undesirable. The reflections are mostly caused by the iris in the eyes, therefore masking the iris area in the eyes is part of the pre-processing prior to sending the masked eye images to pre-trained deep learning model 850 or neural network model 160. The input image to pre-trained deep learning model 850 or neural network model 160 is therefore an eye image that mainly contains sclera details.

Figure 14A:
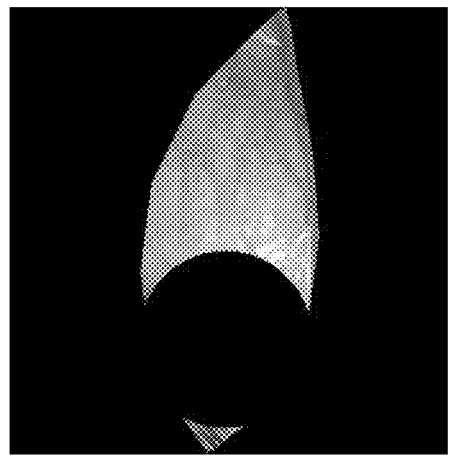
FIG. 14A shows an example of masked eye image with both iris and skin surrounding the eye area masked, in accordance with an embodiment.

FIG. 14A shows an example of masked eye image 1400, with both iris and skin surrounding the eye area masked. The masked eye image 1400 may be generated by pre-processing model 840 or eye data extractor 142 before being transmitted to pre-trained deep learning model 850 or neural network model 160.

Figure 14B:
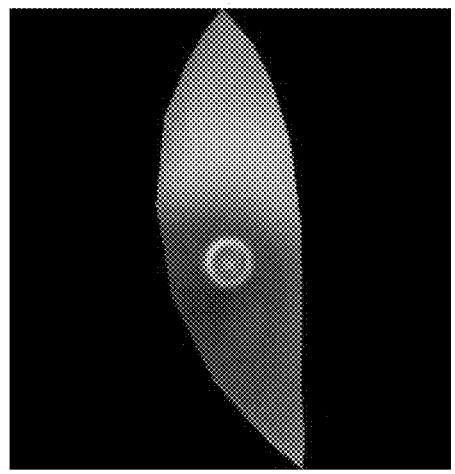
FIG. 14B shows an example of blurred eye image.
Figure 14C:
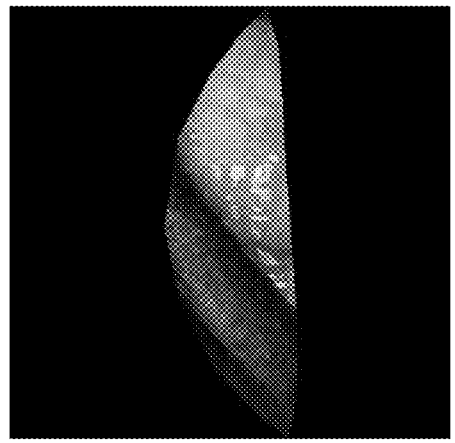
FIG. 14C shows an example of badly cropped eye image.

In some embodiments, extracted eye images are further scanned by a quality-check machine learning model, which may be part of pre-processing, to make sure that they are correctly cropped and have sufficient resolution and sharpness for accurate processing by neural network models 850, 860, 160. For instance, eye size and cropping quality measurement may be checked using a trained model, and Laplacian blur can be used to check the image quality of the extracted eye images. FIG. 14B shows an example of blurred eye image, and FIG. 14C shows an example of badly cropped eye image.

In some embodiments, a size check of the eye within the cropped eye image may be based on a count of total pixels of the extracted eye image on one or two dimensions, to make sure the image contains sufficient information, for instance, a width of the eye in the extracted eye image needs a minimum of 260 pixels in order to pass the eye size check.

The quality-check machine learning model can be a custom-trained deep learning model that outputs a quality score between 0 and 100. To train this model, a mixture of poorly cropped, out-of-focus, and blurred eyes together with high quality eye images that are perfectly cropped without any blurring can be used.

The Laplacian blur check can be based on Laplacian function. The Laplacian of a function f at a point p is (up to a factor) the rate at which the average value of f over spheres centered at p deviates from f(p), as the radius of the sphere shrinks towards 0. A level of blurring, or lack thereof (e.g., smoothness) of an eye image can be qualified and measured based on this Laplacian blur check.

In some embodiments, to ensure the prediction results for the input images are robust and do not trigger false positives or false negatives, a regression model is trained to analyze prediction results compared to given ground truth. The regression model can be implemented to extract one or more rules optimizing true predictions (e.g., true positive or true negative) and simultaneously minimizing the false predictions (false positives and false negatives).

The regression model analyzes and detects the underlying imaging features and environmental variations causing differences between true and false predictions. The significant features via cohort comparison are extracted and a decision tree, to extract the rules coordinating those differences, has been developed. The topmost influencing rules leading to false predictions, either false positive or false negative, are filtered out as part of the pre-processing before any predictions are made using the neural network model 860, 160. Using this step, the main factors that can lead to poor performance like low image quality, blurriness, eye image resolution and color attributes can be detected and filtered out, in order to make an accurate prediction.

A standard deviation check may be implemented in some embodiments to ensure the system 100, 100' including neutral network model 860, 160 is performing well. For each set of tests, the system receives four face images (e.g., with four difference gaze directions), which may be pre-processed to generate eight cropped eye images. Each of the cropped eight eye images is used in a single respective test. Hence, the neutral network model 860, 160 outputs eight predictions, each being a numerical value (e.g., a probability value between 0 and 1 indicating if the user has a certain disease) based on the input set of four face images. A standard deviation check is used for anomaly detection and to ensure that the standard deviation of the output, the eight numerical values, is not significantly different. For instance, if the predication for one or more cropped eye images is/are close to 1.0 (positive) and for the rest is close to 0.0 (negative), the standard deviation would be high, which indicates that the system 100, 100' may have produced uncertain results based on the set of input images, and hence the output is not returned to the user.

In some embodiments, to ensure that all four face images in a set of input images are of the same user or person, a face comparison check is implemented, as part of pre-processing stage, to filter out input images that may be from two different users. For instance, two face feature extraction models can be implemented. Each face feature extraction model can output an embedded vector representing features of the face. For a set of input images having four faces, each image may have a corresponding feature vector. If the feature vectors across four face images have sufficiently close Euclidean distances, the system may consider the images to contain the face of the same user or person.

Different ways of centering the channels of eye images are experimented, during the final step of pre-processing. In one set of experiments, eye images original in RGB format are converted to LAB format, the L channel is zero-centered to adjust brightness, and the B channel is zero-centered to adjust yellowness. In other embodiments, the pre-processing in accordance with TensorFlow is implemented, where each color channel is zero-centered with respect to the ImageNet dataset.

Referring again to FIG. 1, result generator 162 is configured to generate an overall prediction of whether the user has COVID-19 based on the probability metrics generated by neural network 160 for that user. In the depicted embodiment, results generator generates a prediction that the user has COVID-19 if any of the probability metrics is higher than a pre-defined threshold (e.g., 50%, 75% or another suitable threshold). For example, in this embodiment, if any of the eyes yielded a probability metric higher than a 50% threshold, the output of results generator 162 will be "COVID-19 Positive". If none of the eyes yield a probability metric higher than the 50% threshold, the output of results generator 162 will be "COVID-19 Negative".

In other embodiments, result generator 162 may combine the probability metrics in various ways (e.g., by taking a mean value) and compare a combined value against a pre-defined threshold. In some embodiments, the threshold may be adjusted based on the use-case and the acceptability of false positives and false negatives.

Result presenter 108 is configured to present an assessment result to the end user. For example, result presenter 108 may cooperate with HTTP server 110 to provide the assessment result to a device 200 operated by the end user by way of the web application described above. In some embodiments, the presented assessment result provides an indication of whether assessment system 100 has predicted the user to have the target health condition (e.g., COVID-19).

In some embodiments, result generator 162 may present a QR code that can be scanned by another user to obtain information regarding the assessment result, such as the name of the assessed end user and whether that user has been detected to have the target health condition. For example, the QR code may be used by the owner of a commercial establishment such as a restaurant or gym to screen visitors for the target health condition. The effectiveness of the QR code may be limited in time, e.g., for 30 minutes, an hour, or a few hours, after which the QR code can be deactivated. In some embodiments, result generator 162 may direct the end user to install a companion app on device 200 to access the QR code or the assessment result.

HTTP server 110 is an HTTP web server configured to provide a RESTful web application. For example, HTTP server 110 may be implemented using Apache HTTP Server, NGINX, Microsoft IIS or similar server application. HTTP server 110 allows assessment system 100 to act as a conventional HTTP server and provide web pages and a RESTful services for access by way of network-interconnected computing devices (not shown). Web pages may be implemented using traditional web languages such as HTML, XHTML, Java, Javascript, Ruby, Python, Perl, PHP, Flash or the like, and stored in a memory of assessment system 100 (e.g, memory 1304 of FIG. 13). HTTP server 110 may also receive data of images for processing at assessment system 100. In some embodiments, such data may be received by way of a REST API.

Each of image data acquirer 102, image data pre-processor 104, condition predictor 106, result presenter 108, and HTTP server 110 may be implemented using conventional programming languages such as Java, J #, C, C++, C#, Perl, Visual Basic, Ruby, Scala, etc. These components of system 100 may be in the form of one or more executable programs, scripts, routines, statically/dynamically linkable libraries, or the like.

Electronic data store 112 is configured to store data reflective of various model parameters including the trained model of neural network 160. In some embodiments, electronic data store 112 may store image data at various steps of the processing workflow (e.g., the image data received from a device 200, the image data at various steps of pre-processing, etc.) In some embodiments, electronic data store 112 may store results data, i.e., reflecting whether certain patients have tested positive for the target health condition. Electronic data store 112 may be implemented using a combination of non-volatile and volatile memory.

The operation of assessment system 100 for assessing users for COVID-19 is further described with reference to the flowchart depicted in FIG. 9. System 100 performs the example operations depicted at blocks 900 and onward, in accordance with an embodiment.

At block 902, automated guide 120 of assessment system 100 provides automated guidance to the user to obtain the images required for assessment. For example, automated guide 120 guides the user to obtain, by operating his/her device 200, a plurality of images including the user's sclera, where each of the images corresponds to a guided direction of the user's gaze. For example, automated guide 120 may direct the user's gaze to each of center, left, right, and up directions, in sequence. As user's gaze progresses through these different directions, different portions of the user's sclera are imaged. In some embodiments, the order of the directions may vary.

At block 904, data sender/receiver 122 of assessment system 100 causes image data reflecting the obtained images to be sent from device 200 to assessment system 100 by way of network 50. The image data are received at assessment system 100.

At block 906, image data validator 124 of assessment system 100 validates that the images satisfy a plurality of pre-defined requirements. For example, image data validator 124 verifies that the images sufficiently show the user's sclera, including by estimating a direction of the user's gaze and confirming that the estimated direction for a given one of the images conforms with the guided direction corresponding to that image. If the image data validator 124 determines that the one or more of the images do not meet pre-defined requirements, then an error condition is signaled. This signal condition may cause operation of assessment system 100 to return to block 902 so that one or more replacement images may be obtained.

At block 908, image data pre-processor 104 of assessment system 100 applies pre-processing to the validated images. This includes generating feature-enhanced image data by applying an autoencoder to enhance features corresponding to the user's sclera in the images.

Figure 10A:
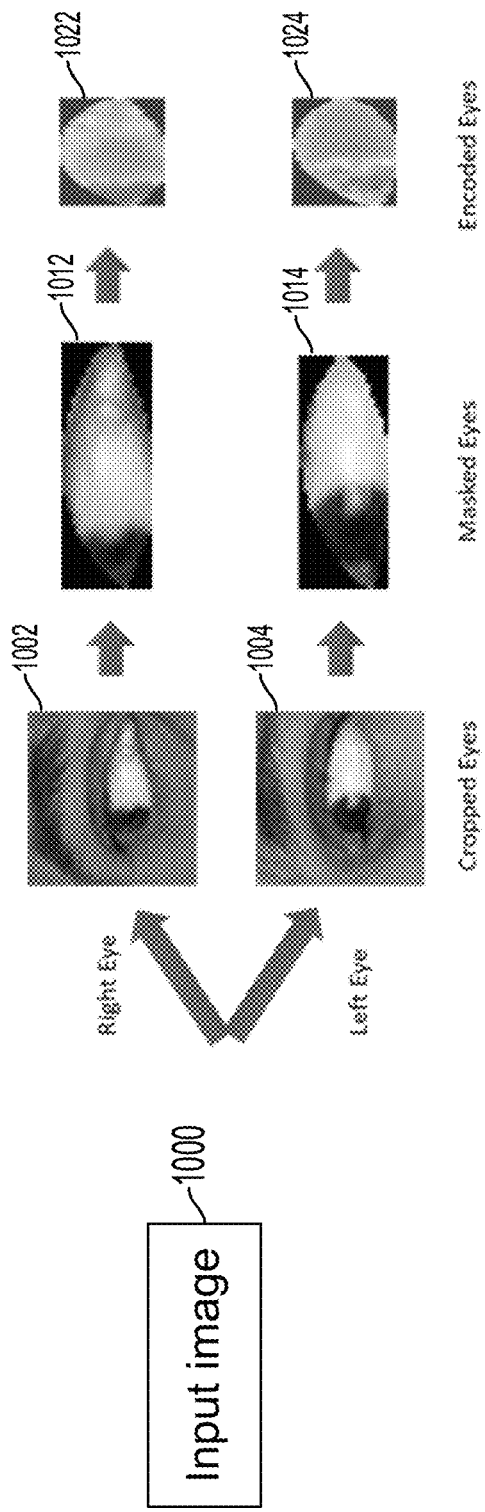
FIG. 10A and FIG. 10B each show example image data during the example operation of FIG. 9, in accordance with an embodiment.

Pre-processing is shown in further detail in FIG. 10A for an example eye image of a user who is COVID-19 negative. In this example, the user is looking in a center direction. As depicted, an input image 1000 is received for pre-processing. Gamma corrector 140 applies gamma correction to image 1000. Next, image whitener 141 applies image whitening to image 1000. Image whitener 141 can check if the image is taken under the yellow light and converts the image color space to LAB. It magnifies the white lighting in the image by decreasing A (Red/Green values) and B (Blue/Yellow values) values proportional to the average pixel values and convert the color space back to RGB from LAB. This process results in a whiter image.

Figure 10B:
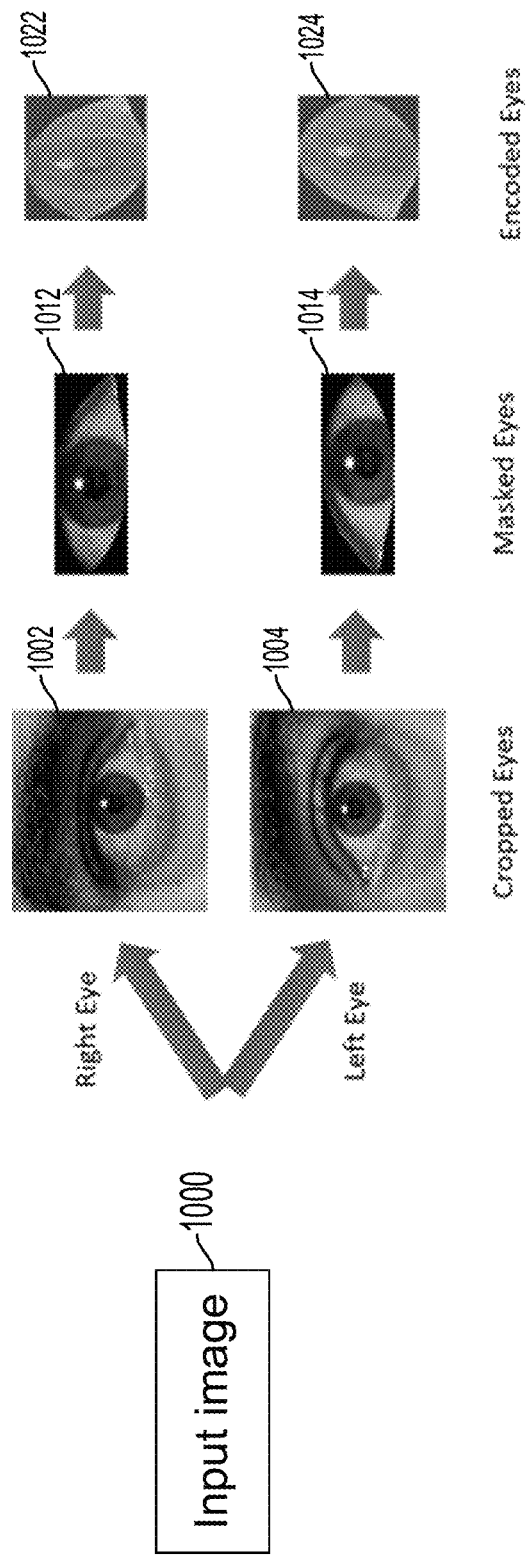

Next, eye data extractor 142 extracts image regions 1002 and 1004 corresponding to the right and left eyes, respectively. Eye data extractor 142 applies masking such that non-eye pixels are set to a value of 0 to provide masked image regions 1012 and 1014 corresponding to the right and left eyes, respectively. Autoencoder 144 then processes each of masked image region 1012 and 1014 to find and enhance relevant features, e.g., features corresponding to the sclera (e.g., ocular manifestations in the sclera attributable to COVID-19). Autoencoder 144 generates feature-enhanced data 1022 and 1024 corresponding to the right and left eyes, respectively. FIG. 10B shows pre-processing for an example eye image of a user who is COVID-19 positive.

Referring again to FIG. 9, at block 912, condition predictor 106 computes a prediction of whether the user has the target health condition by providing the feature-enhanced image data to neural network 160. The prediction may be generated by results generator 162 using the outputs of neural network 160.

Following block 912, the prediction result may be presented to the user by results presenter 108, e.g., by transmitting the result to the user's device 200.

Figure 9:
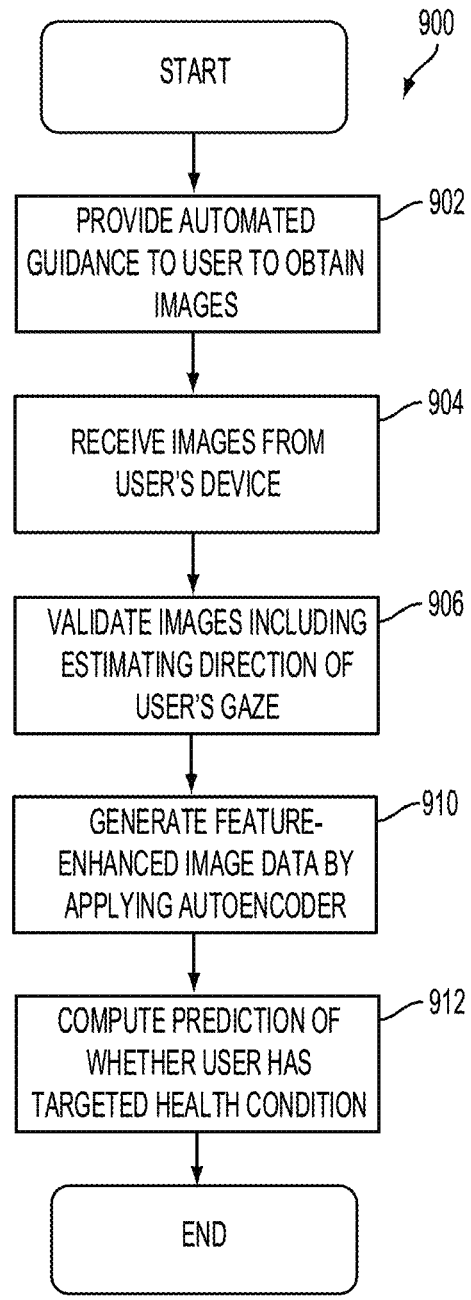
FIG. 9 is a flowchart showing example operation of the system of FIG. 1, in accordance with an embodiment.

It should be understood that steps of one or more of the blocks depicted in FIG. 9 may be performed in a different sequence or in an interleaved or iterative manner. Further, variations of the steps, omission or substitution of various steps, or additional steps may be considered.

Figure 11:
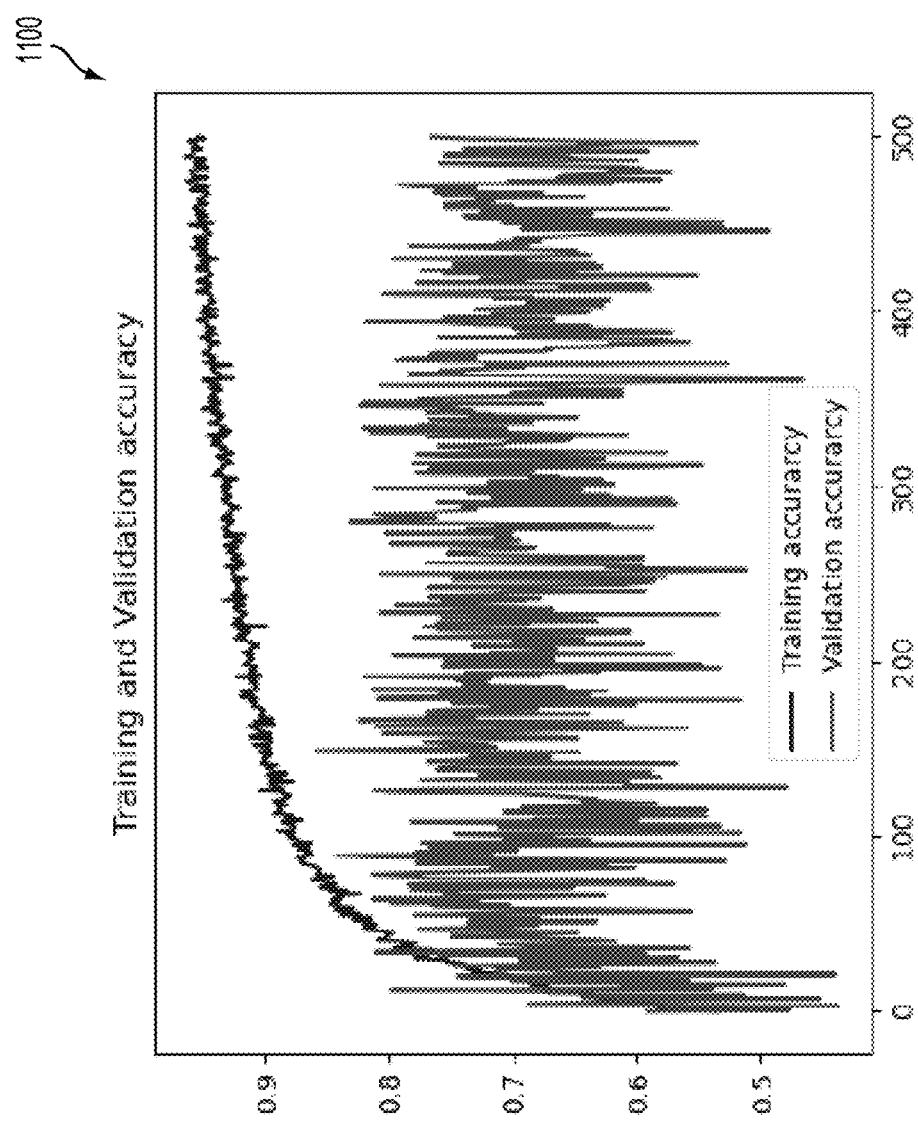
FIG. 11 is a graph showing assessment performance characteristics of the system of FIG. 1 in accordance with an embodiment.

FIG. 11 is a graph 1100 showing assessment performance characteristics for an example embodiment of assessment system 100 configured for assessing COVID-19. This embodiment was trained using 1635 COVID-19 positive training images and 1488 COVID-19 negative training images. A training-validation split ratio of approximate 0.2 was used. As depicted in FIG. 11, this embodiment provides a specificity of 82% and a sensitivity of 73%.

In the foregoing, embodiments of assessment system 100 have been described for the detection of whether a user has COVID-19. In other embodiments, assessment system 100 may be adapted for assessment of other health conditions such as diseases caused by other coronaviruses or other viruses that cause ocular manifestations. In other embodiments, assessment system 100 may be adapted for assessment of an ocular condition such as conjunctivitis, pink eye, cataracts, glaucoma, bulging eyes, uveitis, and ocular herpes, or the like.

In some embodiments, assessment system 100 may be adapted for usage to screen users passing through an entrance or checkpoint (e.g., at airports, shopping malls, offices, or the like). In such situations assessment system 100 may receive eye image data from a workstation (e.g., a desktop computer) interconnected with an IR camera disposed to image the users at the entrance or checkpoint.

Figure 12:
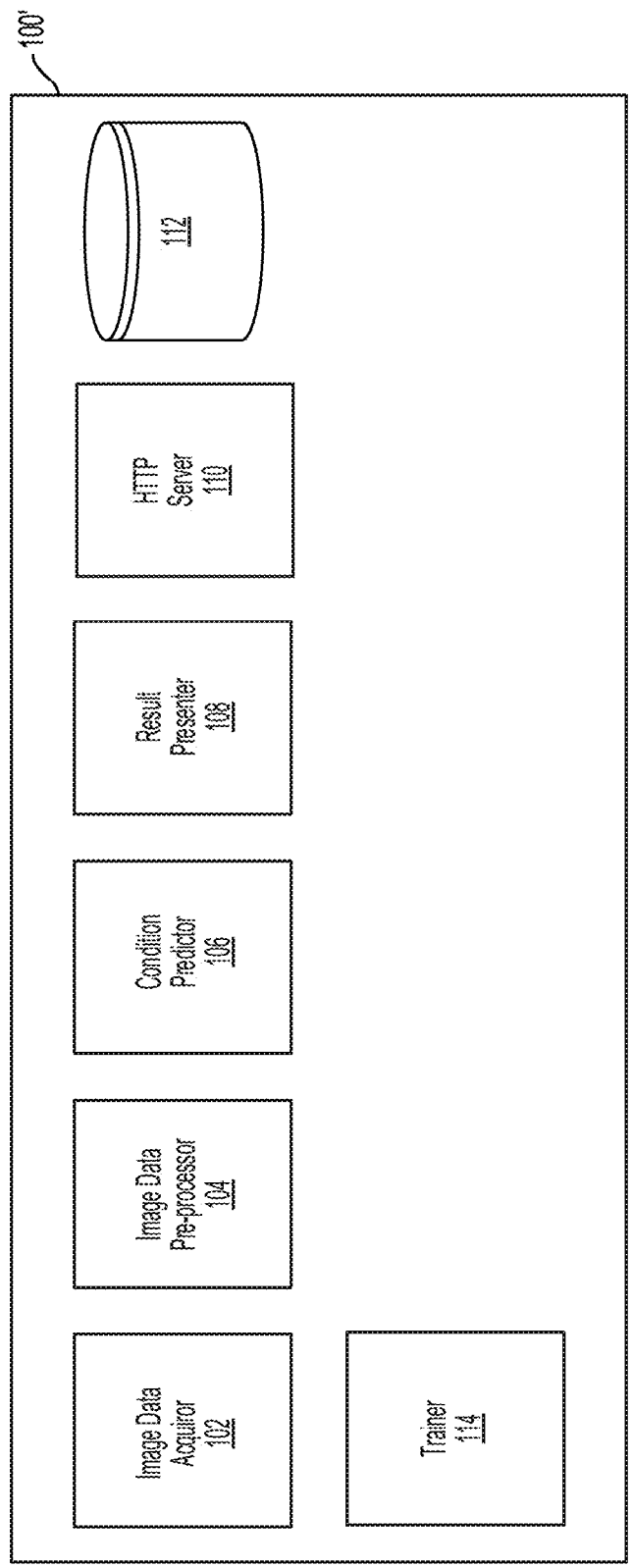
FIG. 12 is a schematic diagram of another example system for remote assessment of a target health condition, in accordance with an embodiment.

FIG. 12 is a schematic diagram of an assessment system 100', in accordance with an embodiment. Assessment system 100' is substantially similar to assessment system 100, but additionally includes a trainer 114. Trainer 114 is configured to train further neural network 160 based on data obtained during operation of system 100'.

In this embodiment, image data received from a user may be stored at assessment system 100' (e.g., in electronic data store 112) to be used as training data. The image data is labeled, e.g., based on test results obtained for a user via RT-PCR tests as self-reported by the user. The image data and labels may be stored anonymously at assessment system 100' to protect user privacy.

Trainer 114 uses the labeled image data as training data to train neural network 160. Various conventional training algorithms may be used. In this way, the performance of neural network 160 may be improved over time.

In some embodiments, trainer 114 is configured to train further components of assessment system 100'. For example, trainer 114 may be configured to train autoencoder 144, and thereby improve its performance over time.

Assessment system 100' is otherwise substantially similar to assessment system 100.

Training of Neural Network 160, 860

To train neural network model 160, 860, four face images, each with a respective gazing direction, are given to neural network model 160, 860 as input data for neural network model 160, 860 to generate an output indicating a prediction based on the eye areas within the images. In the four face images, the user is shown with his or her gaze towards a respective direction in each image: center, left, right, and up. The face images each includes the entire face of the user, such that a face recognition model may extract the face image therein. The user should be located a relatively close distance to the camera, so their face can occupy most of the image frame (boundary), such that their eye areas are sufficiently large and contain enough pixel data. As elaborated above in detail, the input face images are checked and pre-processed prior to being sent to neural network model 160, 860 for training. A face recognition model locates the face in each image and based on the coordinates of the iris, eye corners, and eyelids, the user's gaze direction in each image can be verified. If the four face images are all verified by the face recognition model, eight individual eye areas in the four images are cropped based on the coordinates of the eye areas.

To ensure that neural network model 160, 860 sees both high- and low-quality images, different phone cameras were used, during training, for input image collection. For example, iPhone™ 13 Pro Max and iPhone™ 12 Pro back cameras were used for taking high-quality images, while the front-facing cameras of another brand were used for taking relatively low-quality images. All these cameras are at a minimum 5MP quality (e.g., producing images with a resolution of 2,560×1,920 pixels per unit), which is a minimum requirement for taking images of decent quality.

Three data sources are used for training neural network model 160, 860. The first data source is from Curebase, which is an independent Clinical Research Organization (CRO) that has contracted 11 clinical research sites across the United States, the sites enrolled participants who visited a COVID-19 testing center, and the participants were surveyed and their data recorded using double ground truth benchmarks of PCR and Antigen tests. For each participant, face images were collected within 3 days from taking a traditional Antigen or PCR Test. Each participant had follow-up visits scheduled on Day 15 and 21 based on a negative Antigen test. The collected images were taken with the iPhone™ 13 Pro Max back camera and the Samsung™ S9 camera.

The second data source, JHS dataset, is collected in the emergency department of Jackson Memorial Hospital. There are three different cameras in the dataset: iPhone™ 13 Pro Max back camera, iPhone™ 8 front camera, and Samsung™ S9 front camera. The images are collected in the emergency rooms and contain both positive and negative patients with a variety of different ages, genders, and ethnicity groups.

The third data source, KEI dataset, is collected at Kensington Eye Institute. There are two cameras used: iPhone™ 12 and Samsung™ S8. There are two groups of population in this dataset. The first one is healthy COVID-19 negative patients with no ocular diseases and the second one is COVID-19 negative patients with one or more ocular diseases, which are referred as "ocular negatives" in this disclosure. The ocular negative group images were not used for training and were only used during test of trained neural network model 160, 860.

Below is a collection of training dataset used for training example embodiments of neural network model 160, 860. The training was done with randomly splitting training and validation set with the ratio of 80/20. It was repeated a number of times and the neural network model with the best validation result was selected. The patients (users) in the training set have been selected in a way to well represent a target population and to ensure robustness of the trained models. Moreover, all measures were in place to ensure the training set has no bias and can achieve heterogeneity.

TABLE 1

| | Training Set | |
|---|---|---|
| Cohort | Images [Positive/ Negative (Total)] | Tests [Positive/ Negative (Total)] |
| Curebase (Positives) | 242/0 (242) | 81/0 (81) |
| JHS (Positive + Negative) | 703/1220 (1923) | 190/332 (522) |
| KEI (Healthy Negatives) | 0/1012 (1012) | 0/208 (208) |
| Overall | 945/2232 (3177) | 271/540 (811) |

As shown in table 1, a training set has 945 images in the COVID-19 positive class and 2,232 images in the negative class.

In the following tables, column notations are as follows:

Yes (P): has symptoms and is COVID Positive

No (P): does not have symptoms and is COVID Positive

Yes (N): has symptoms and is COVID Negative

No (N): does not have symptoms and is COVID Negative

NA (P): not specified and is COVID Positive

NA (N): not specified and is COVID Negative

TABLE 2

| Overall training set symptoms distribution | | | | | | |
|---|---|---|---|---|---|---|
| Overall | Yes (P) | No (P) | Yes (N) | No (N) | NA (P) | NA (N) |
| Temperature ≥ 37.5 | 84 | 130 | 0 | 528 | 57 | 12 |
| Ocular pain | 32 | 161 | 0 | 528 | 78 | 12 |
| Ocular discharge | 4 | 183 | 0 | 528 | 84 | 12 |
| Red eyes (conjunctivitis) | 20 | 173 | 0 | 529 | 78 | 11 |
| Foreign body sensation | 8 | 179 | 0 | 532 | 84 | 8 |
| Dry eye | 18 | 172 | 0 | 535 | 81 | 5 |
| Blurred vision | 26 | 165 | 0 | 535 | 80 | 5 |
| Eye itching | 19 | 173 | 0 | 535 | 79 | 5 |
| Swelling of the white part of the eye (Chemosis) | 7 | 179 | 0 | 535 | 85 | 5 |
| Watery eyes (Epiphora) | 18 | 171 | 0 | 535 | 82 | 5 |
| Swollen eyelids | 8 | 184 | 0 | 535 | 79 | 5 |
| Rash on eyelid (Eyelid dermatitis) | 2 | 185 | 0 | 535 | 84 | 5 |
| Cough | 168 | 85 | 0 | 535 | 18 | 5 |
| Sore throat or cold | 127 | 114 | 0 | 535 | 30 | 5 |
| Headache | 133 | 108 | 0 | 535 | 30 | 5 |
| Diarrhea and/or vomit | 72 | 126 | 0 | 535 | 73 | 5 |
| Weakness or muscular pain | 124 | 108 | 0 | 535 | 39 | 5 |
| Loss of smell | 22 | 171 | 0 | 531 | 78 | 9 |
| Loss of taste | 29 | 167 | 0 | 529 | 75 | 11 |

TABLE 3

Overall training set gender distribution

| Gender | Male (P) | Female (P) | Male (N) | Female (N) | NA (P) | NA (N) |
|---|---|---|---|---|---|---|
| Count | 116 | 151 | 187 | 344 | 4 | 9 |

TABLE 4

Overall training set age group distribution

| Age Group | Positive | Negative |
|---|---|---|
| Age <40 | 104 | 141 |
| Age >39, <60 | 87 | 189 |
| Age >=60 | 76 | 198 |
| Age (NA) | 4 | 12 |
| Total | 271 | 540 |

TABLE 5

Overall test set ethnicity distribution

| Ethnicity | Positive | Negative |
|---|---|---|
| White | 88 | 123 |
| Black | 42 | 67 |
| NA | 7 | 15 |
| Asian | 9 | 89 |
| Native Hawaiian or Other Pacific Islander | 1 | 0 |
| Hispanic | 116 | 233 |
| American Indian or Alaska Native | 2 | 0 |
| Bahamas | 0 | 2 |
| Mixed Origin | 4 | 2 |
| Bangladesh | 2 | 0 |
| European | 0 | 3 |
| Portuguese | 0 | 4 |
| Middle eastern north African | 0 | 1 |
| Scottish | 0 | 1 |
| Total | 271 | 540 |

Analysis Per Cohort Dataset

Curebase Dataset (Only Positives):

TABLE 6

Curebase training set symptoms distribution

| Curebase (Positives, 81 cases) | Yes(P) | NA(P) |
|---|---|---|
| Temperature ≥37.5 | 27 | 54 |
| Ocular pain | 6 | 75 |
| Ocular discharge | 0 | 81 |
| Red eyes (conjunctivitis) | 6 | 75 |
| Foreign body sensation | 0 | 81 |
| Dry eye | 3 | 78 |
| Blurred vision | 4 | 77 |
| Eye itching | 5 | 76 |
| Swelling of the white part of the eye (Chemosis) | 0 | 81 |
| Watery eyes (Epiphora) | 2 | 79 |
| Swollen eyelids | 5 | 76 |
| Rash on eyelid (Eyelid dermatitis) | 0 | 81 |
| Cough | 66 | 15 |
| Sore throat or cold | 54 | 27 |
| Headache | 54 | 27 |
| Diarrhea and/or vomit | 11 | 70 |
| Weakness or muscular pain | 45 | 36 |
| Loss of smell | 6 | 75 |
| Loss of taste | 9 | 72 |

TABLE 7

Curebase training set gender distribution

| Gender (Curebase) | Male(P) | Female(P) | NA(P) |
|---|---|---|---|
| Count | 35 | 45 | 1 |

TABLE 8

Curebase training set age group distribution

| Age Group (Curebase) | Count |
|---|---|
| Age <40 | 46 |
| Age >39, <60 | 30 |
| Age >=60 | 4 |
| Age (NA) | 1 |
| Total | 81 |

TABLE 9

Curebase training set ethnicity distribution

| Ethnicity (Curebase) | Count |
|---|---|
| White | 61 |
| Black | 5 |
| NA | 4 |
| Asian | 8 |
| Native Hawaiian or Other Pacific Islander | 1 |
| American Indian or Alaska Native | 2 |

JHS Dataset (Positives and Negatives):

TABLE 10

JHS training set symptoms distribution

| JHS (190 Positives, 332 Negatives) | Yes (P) | No (P) | Yes (N) | No (N) | NA (P) | NA (N) |
|---|---|---|---|---|---|---|
| Temperature ≥ 37.5 | 57 | 130 | 0 | 324 | 3 | 8 |
| Ocular pain | 26 | 161 | 0 | 324 | 3 | 8 |
| Ocular discharge | 4 | 183 | 0 | 324 | 3 | 8 |
| Red eyes (conjunctivitis) | 14 | 173 | 0 | 321 | 3 | 11 |
| Foreign body sensation | 8 | 179 | 0 | 324 | 3 | 8 |
| Dry eye | 15 | 172 | 0 | 327 | 3 | 5 |
| Blurred vision | 22 | 165 | 0 | 327 | 3 | 5 |
| Eye itching | 14 | 173 | 0 | 327 | 3 | 5 |
| Swelling of the white part of the eye (Chemosis) | 7 | 179 | 0 | 327 | 4 | 5 |
| Watery eyes (Epiphora) | 16 | 171 | 0 | 327 | 3 | 5 |
| Swollen eyelids | 3 | 184 | 0 | 327 | 3 | 5 |
| Rash on eyelid (Eyelid dermatitis) | 2 | 185 | 0 | 327 | 3 | 5 |
| Cough | 102 | 85 | 0 | 327 | 3 | 5 |
| Sore throat or cold | 73 | 114 | 0 | 327 | 3 | 5 |
| Headache | 79 | 108 | 0 | 327 | 3 | 5 |
| Diarrhea and/or vomit | 61 | 126 | 0 | 327 | 3 | 5 |
| Weakness or muscular pain | 79 | 108 | 0 | 327 | 3 | 5 |
| Loss of smell | 16 | 171 | 0 | 327 | 3 | 5 |
| Loss of taste | 20 | 167 | 0 | 327 | 3 | 5 |

TABLE 11

JHS training set gender distribution

| Gender (JHS) | Male (P) | Female (P) | Male (N) | Female (N) | NA (P) | NA (N) |
|---|---|---|---|---|---|---|
| Count | 81 | 106 | 116 | 211 | 3 | 5 |

TABLE 12

JHS training set age group distribution

| Age Group (JHS) | Positive | Negative |
|---|---|---|
| Age <40 | 58 | 61 |
| Age >39, <60 | 57 | 126 |
| Age >=60 | 72 | 137 |
| Age (NA) | 3 | 8 |
| Total | 190 | 332 |

TABLE 13

JHS training set ethnicity distribution

| Ethnicity (JHS) | Positive | Negative |
|---|---|---|
| White | 27 | 35 |
| Black | 37 | 51 |
| NA | 3 | 11 |
| Asian | 1 | 7 |
| Hispanic | 116 | 226 |
| Bahamas | 0 | 2 |
| Mixed Origin | 4 | 0 |
| Bangladesh | 2 | 0 |
| Total | 190 | 332 |

KEI Dataset (Only Healthy Negatives):

TABLE 14

KEI training set symptoms distribution

| KEI (Negatives 208) | No(N) | NA(N) |
|---|---|---|
| Temperature ≥37.5 | 204 | 4 |
| Ocular pain | 204 | 4 |
| Ocular discharge | 204 | 4 |
| Red eyes (conjunctivitis) | 208 | 0 |
| Foreign body sensation | 208 | 0 |
| Dry eye | 208 | 0 |
| Blurred vision | 208 | 0 |
| Eye itching | 208 | 0 |
| Swelling of the white part of the eye (Chemosis) | 208 | 0 |
| Watery eyes (Epiphora) | 208 | 0 |
| Swollen eyelids | 208 | 0 |
| Rash on eyelid (Eyelid dermatitis) | 208 | 0 |
| Cough | 208 | 0 |
| Sore throat or cold | 208 | 0 |
| Headache | 208 | 0 |
| Diarrhea and/or vomit | 208 | 0 |
| Weakness or muscular pain | 208 | 0 |
| Loss of smell | 204 | 4 |
| Loss of taste | 202 | 6 |

TABLE 15

KEI training set gender distribution

| Gender (KEI) | Male(N) | Female(N) | NA(N) |
|---|---|---|---|
| Count | 71 | 133 | 4 |

TABLE 16

KEI training set age group distribution

| Age Group (KEI) | Count |
|---|---|
| Age <40 | 80 |
| Age >39, <60 | 63 |
| Age >=60 | 61 |
| Age (NA) | 4 |
| Total | 208 |

TABLE 17

KEI training set ethnicity distribution

| Ethnicity (KEI) | Count |
|---|---|
| White | 88 |
| Black | 16 |
| NA | 4 |
| Asian | 82 |
| Hispanic | 7 |
| Mixed Origin | 2 |
| European | 3 |
| Portuguese | 4 |
| Middle eastern north African | 1 |
| Scottish | 1 |
| Total | 208 |

After the example embodiments of neural network model 160, 860 has been trained, at inference time, eight eye images with masked iris are transmitted to neural network model 160, 860, and the mean of the model predictions are computed. Within a threshold of 0.5, all metrics including accuracy, sensitivity, and specificity are calculated. The test dataset with masked iris and the following distributions were used for model evaluation.

TABLE 18

Test set with masked iris
Test Set with Masked Iris

| Cohort | Images [P/N (Total)] | Tests [P/N (Total)] | Unique Patients [P/N (Total)] |
|---|---|---|---|
| Curebase (Positives) | 552/0 (552) | 69/0 (69) | 64/0 (64) |
| JHS (Positives + Negatives) | 256/256 (512) | 32/32 (64) | 32/32 (64) |
| KEI (Ocular Negatives) | 0/736 (736) | 0/92 (92) | 0/92 (92) |
| Overall | 808/992 (1800) | 101/124 (225) | 96/124 (220) |

The following description contains various diagrams and tables illustrating the analysis of the test set heterogeneity and its characteristics.

In the following table, column notations are as follows:

Yes (P): has symptoms and is COVID Positive

No (P): does not have symptoms and is COVID Positive

Yes (N): has symptoms and is COVID Negative

No (N): does not have symptoms and is COVID Negative

NA (P): not specified and is COVID Positive

NA (N): not specified and is COVID Negative

TABLE 19

Overall tests et symptoms distribution

| Symptoms (P: 101, N: 124, Total 225 Cases) | Yes (P) | No (P) | Yes (N) | No (N) | NA (P) | NA (N) |
|---|---|---|---|---|---|---|
| Temperature ≥ 37.5 | 33 | 18 | 0 | 123 | 50 | 1 |
| Ocular pain | 13 | 21 | 2 | 121 | 67 | 1 |
| Ocular discharge | 5 | 27 | 1 | 122 | 69 | 1 |
| Red eyes (conjunctivitis) | 6 | 27 | 1 | 122 | 68 | 1 |
| Foreign body sensation | 3 | 29 | 1 | 122 | 69 | 1 |
| Dry eye | 5 | 29 | 1 | 122 | 67 | 1 |
| Blurred vision | 9 | 25 | 1 | 122 | 67 | 1 |
| Eye itching | 9 | 28 | 2 | 121 | 64 | 1 |
| Swelling of the white part of the eye (Chemosis) | 0 | 29 | 0 | 123 | 72 | 1 |
| Watery eyes (Epiphora) | 18 | 24 | 1 | 122 | 59 | 1 |
| Swollen eyelids | 2 | 28 | 2 | 121 | 71 | 1 |
| Rash on eyelid (Eyelid dermatitis) | 0 | 29 | 0 | 123 | 72 | 1 |
| Cough | 80 | 9 | 2 | 120 | 12 | 2 |
| Sore throat or cold | 57 | 16 | 0 | 123 | 28 | 1 |
| Headache | 65 | 17 | 1 | 122 | 19 | 1 |
| Diarrhea and/or vomit | 31 | 23 | 2 | 120 | 47 | 2 |
| Weakness or muscular pain | 68 | 11 | 3 | 120 | 22 | 1 |
| Loss of smell | 19 | 27 | 0 | 123 | 55 | 1 |
| Loss of taste | 18 | 28 | 0 | 123 | 55 | 1 |

TABLE 20

Overall test set gender distribution

| Gender (Overall) | Male (P) | Female (P) | Male (N) | Female (N) | NA (P) | NA (N) |
|---|---|---|---|---|---|---|
| Count | 37 | 61 | 46 | 77 | 3 | 1 |

TABLE 21

Overall test set age group distribution

| Age Group (Overall) | Positive | Negative |
|---|---|---|
| Age <40 | 43 | 7 |
| Age >39, <60 | 33 | 26 |
| Age >=60 | 22 | 88 |
| Age (N/A) | 3 | 3 |
| Total | 101 | 124 |

TABLE 22

Overall test set ethnicity distribution

| Ethnicity (Overall) | Positive | Negative |
|---|---|---|
| White | 56 | 69 |
| Black | 9 | 6 |
| N/A | 12 | 1 |
| Asian | 3 | 19 |
| Native Hawaiian or Other Pacific Islander | 1 | 0 |
| Hispanic | 19 | 28 |
| Indigenous | 1 | 1 |

Distribution per cohort database are illustrated below.

Curebase Statistics:

TABLE 23

Curebase test set symptoms distribution

| Symptoms (Curebase, P: 69) | Yes | NA |
|---|---|---|
| Temperature ≥37.5 | 22 | 47 |
| Ocular pain | 5 | 64 |
| Ocular discharge | 3 | 66 |
| Red eyes (conjunctivitis) | 4 | 65 |
| Foreign body sensation | 3 | 66 |
| Dry eye | 5 | 64 |
| Blurred vision | 5 | 64 |
| Eye itching | 8 | 61 |
| Swelling of the white part of the eye (Chemosis) | 0 | 69 |
| Watery eyes (Epiphora) | 13 | 56 |
| Swollen eyelids | 1 | 68 |
| Rash on eyelid (Eyelid dermatitis) | 0 | 69 |
| Cough | 60 | 9 |
| Sore throat or cold | 44 | 25 |
| Headache | 53 | 16 |
| Diarrhea and/or vomit | 25 | 44 |
| Weakness or muscular pain | 50 | 19 |
| Loss of smell | 17 | 52 |
| Loss of taste | 17 | 52 |

TABLE 24

Curebase test set gender distribution

| Gender (Curebase) | Male | Female |
|---|---|---|
| Count | 22 | 47 |

TABLE 25

Curebase test set age group distribution

| Age Group (Curebase) | Count |
|---|---|
| Age <40 | 37 |
| Age >39, <60 | 23 |
| Age >=0 | 9 |

TABLE 26

Curebase test set ethnicity distribution

| Ethnicity (Curebase) | Count |
|---|---|
| White | 51 |
| Black | 5 |
| N/A | 9 |
| Asian | 3 |
| Native Hawaiian or Other Pacific Islander | 1 |
| Hispanic | 0 |
| Indigenous | 0 |

JHS Statistics:

TABLE 27

JHS test set symptoms distribution

| Symptoms (JHS P: 32, N: 32, Total 64 Cases) | Yes (P) | No (P) | Yes (N) | No (N) | NA (P) | NA (N) |
|---|---|---|---|---|---|---|
| Temperature ≥ 37.5 | 11 | 18 | 0 | 32 | 3 | 0 |
| Ocular pain | 8 | 21 | 1 | 31 | 3 | 0 |
| Ocular discharge | 2 | 27 | 0 | 32 | 3 | 0 |
| Red eyes (conjunctivitis) | 2 | 27 | 0 | 32 | 3 | 0 |
| Foreign body sensation | 0 | 29 | 0 | 32 | 3 | 0 |
| Dry eye | 0 | 29 | 0 | 32 | 3 | 0 |
| Blurred vision | 4 | 25 | 0 | 32 | 3 | 0 |
| Eye itching | 1 | 28 | 1 | 31 | 3 | 0 |
| Swelling of the white part of the eye (Chemosis) | 0 | 29 | 0 | 32 | 3 | 0 |
| Watery eyes (Epiphora) | 5 | 24 | 0 | 32 | 3 | 0 |
| Swollen eyelids | 1 | 28 | 1 | 31 | 3 | 0 |
| Rash on eyelid (Eyelid dermatitis) | 0 | 29 | 0 | 32 | 3 | 0 |
| Cough | 20 | 9 | 2 | 30 | 3 | 0 |
| Sore throat or cold | 13 | 16 | 0 | 32 | 3 | 0 |
| Headache | 12 | 17 | 1 | 31 | 3 | 0 |
| Diarrhea and/or vomit | 6 | 23 | 2 | 30 | 3 | 0 |
| Weakness or muscular pain | 18 | 11 | 2 | 30 | 3 | 0 |
| Loss of smell | 2 | 27 | 0 | 32 | 3 | 0 |
| Loss of taste | 1 | 28 | 0 | 32 | 3 | 0 |

TABLE 28

JHS test set gender distribution

| Gender (JHS) | Male (P) | Female (P) | Male (N) | Female (N) | NA (P) | NA (N) |
|---|---|---|---|---|---|---|
| Count | 15 | 14 | 11 | 21 | 3 | 0 |

TABLE 29

JHS test set age group distribution

| Age Group (JHS) | Positive (P) | Negative (N) |
|---|---|---|
| Age <40 | 6 | 4 |
| Age >39, <60 | 10 | 21 |
| Age >=60 | 13 | 7 |
| Age (NA) | 3 | 0 |

TABLE 30

JHS test set ethnicity distribution

| Ethnicity (JHS) | Positive (P) | Negative (N) |
|---|---|---|
| White | 5 | 2 |
| Black | 4 | 3 |
| NA | 3 | 0 |
| Asian | 0 | 0 |
| Native Hawaiian or Other Pacific Islander | 0 | 0 |
| Hispanic | 19 | 26 |
| Indigenous | 1 | 1 |

KEI Ocular Negatives Statistics:

TABLE 31

KEI test set symptoms distribution

| Symptoms (KEI Ocular Negatives, Total 92 Cases) | Yes(N) | No(N) |
|---|---|---|
| Temperature ≥37.5 | 0 | 91 |
| Ocular pain | 1 | 90 |
| Ocular discharge | 1 | 90 |
| Red eyes (conjunctivitis) | 1 | 90 |
| Foreign body sensation | 1 | 90 |
| Dry eye | 1 | 90 |
| Blurred vision | 1 | 90 |
| Eye itching | 1 | 90 |
| Swelling of the white part of the eye (Chemosis) | 0 | 91 |
| Watery eyes (Epiphora) | 1 | 90 |
| Swollen eyelids | 1 | 90 |
| Rash on eyelid (Eyelid dermatitis) | 0 | 91 |
| Cough | 0 | 90 |
| Sore throat or cold | 0 | 91 |
| Headache | 0 | 91 |
| Diarrhea and/or vomit | 0 | 90 |
| Weakness or muscular pain | 1 | 90 |
| Loss of smell | 0 | 91 |
| Loss of taste | 0 | 91 |

TABLE 32

KEI test set gender distribution

| Gender (KEI Ocular Negatives) | Male (N) | Female (N) | NA (N) |
|---|---|---|---|
| Count | 35 | 56 | 1 |

TABLE 33

KEI test set age group distribution

| Age Group (KEI Ocular Negatives) | Count |
|---|---|
| Age <40 | 3 |
| Age >39, <60 | 5 |
| Age >=60 | 81 |
| Age (NA) | 3 |

TABLE 34

KEI test set ethnicity distribution

| Ethnicity (KEI Ocular Negatives) | Count |
|---|---|
| White | 67 |
| Black | 3 |
| NA | 1 |
| Asian | 19 |
| Native Hawaiian or Other Pacific Islander | 0 |
| Hispanic | 2 |
| Indigenous | 0 |

Model Performance

To evaluate performance of trained neural network model 160, 860, a realistic test set that includes most of the cases that neural network model 160, 860 would face in the real world. The final test set has images from Curebase positive cohort, JHS positive and negatives, and KEI ocular negatives (patients with one or more ocular diseases like Cataracts, Glaucoma, etc.). Samples of KEI ocular negatives were not used in the training, and the fact that the trained neural network model 160, 860 has not seen these eye conditions before makes the prediction more realistic and also more difficult.

Figure 15A:
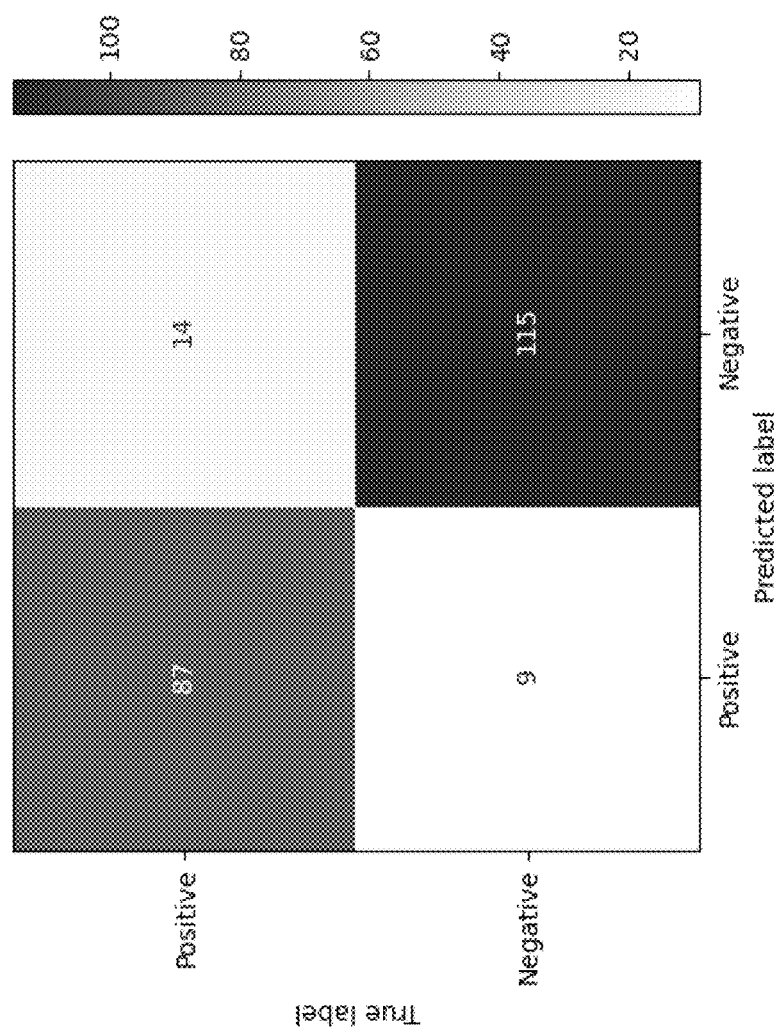
FIG. 15A shows a COVID-19 classifier confusion matrix based on the model performance of trained neural network model, in accordance with an embodiment.
Figure 15B:
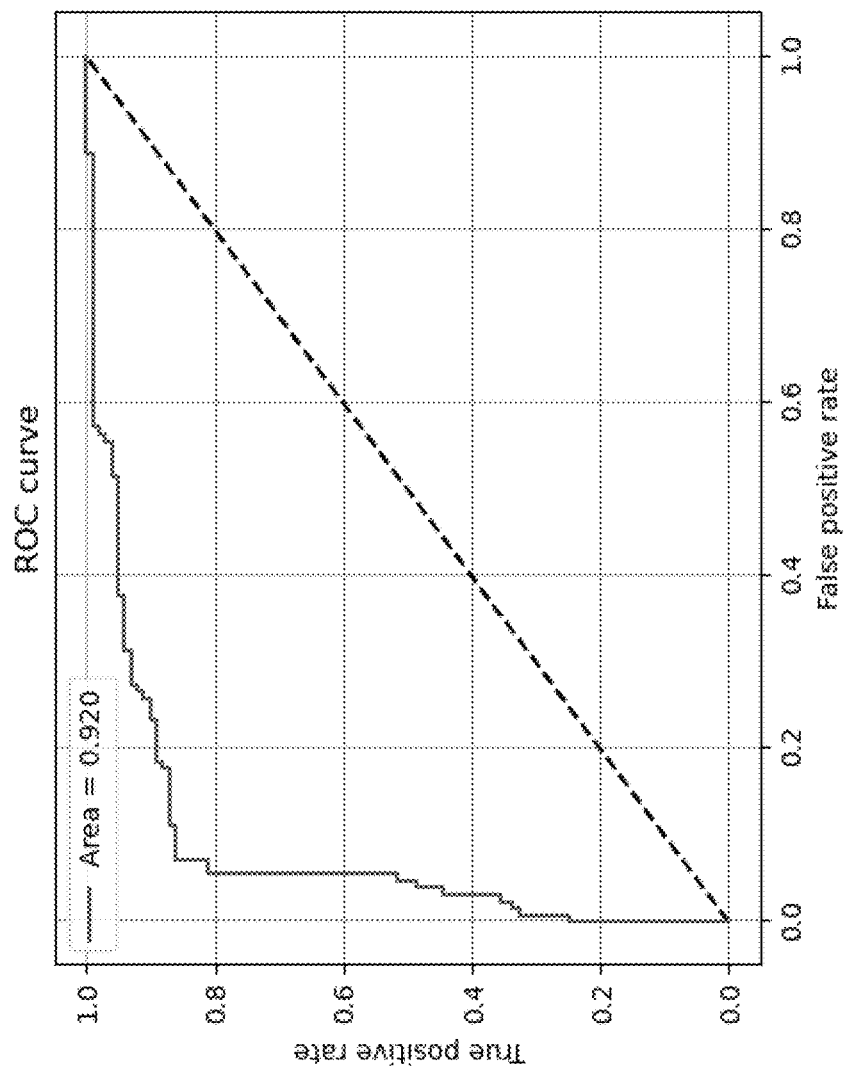
FIG. 15B shows a COVID-19 classifier ROC curve matrix based on the model performance of trained neural network model, in accordance with an embodiment.

FIG. 15A shows a COVID-19 classifier confusion matrix based on the model performance of trained neural network model 160, 860, FIG. 15B shows a COVID-19 classifier ROC curve matrix based on the model performance of neural network model 160, 860, and table 35 below shows data relating to the model performance.

TABLE 35

COVID-19 Model Performance

| Cohort | Accuracy | Sensitivity | Specificity |
| --- | --- | --- | --- |
| Curebase (Positives) | 0.87 | 0.87 | N/A |
| JHS (Positives + Negatives) | 0.88 | 0.84 | 0.91 |
| KEI (Ocular Negatives) | 0.93 | N/A | 0.93 |
| Overall | 0.90 | 0.86 | 0.93 |

To better understand how the model makes a prediction on an image, Grad-CAM analysis was performed. Gradient-weighted Class Activation Mapping (Grad-CAM) is a technique that uses the gradients of the final convolutional layer of a network (with respect to each of its output nodes) to produce a coarse localization map that highlights the important regions in the image for predicting the corresponding class. FIGS. 16A and 16B depict a few of these Grad-CAM maps overlaid on top of the original images. FIG. 16A illustrates the Grad-CAM maps for eye images that were predicted as COVID-19 positive and FIG. 16B illustrates the Grad-CAM maps for eye images predicted as COVID-19 negative.

In each of the Grad-CAM images shown in FIGS. 16A and 16B, the most important regions are depicted in red followed by yellow, green, and blue.

Figure 17:
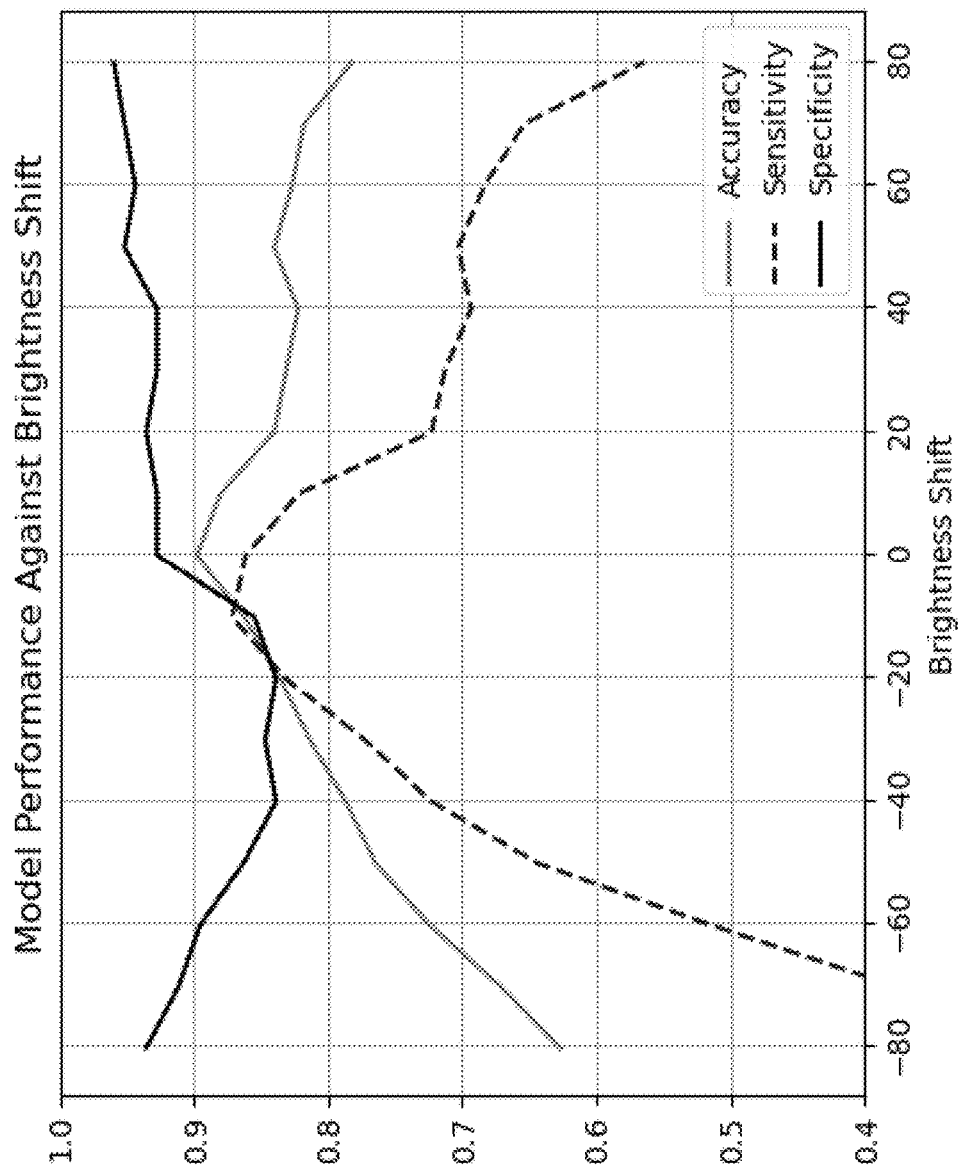
FIG. 17 shows a chart of neural network model performance metric due to a shift in brightness value in the images.

Further testing of neural network model 160, 860 revealed that the brightness intensity had a determining factor in classifying images as COVID-19 positive or negative. Therefore, a series of studies were undertaken to measure the impact of brightness on the consistency and robustness of the predictions. As a result, the brightness of the test set images is adjusted in the range of [−80:10:80]. FIG. 17 shows the neural network model performance metrics due to a shift in brightness value in the images, which is presented as a plot of accuracy, sensitivity, and specificity against changes in brightness. FIG. 17 shows that model performance is somewhat stable within the usable brightness range [−20 to +10].

To boost the model performance and to improve the accuracy of prediction, an experiment was conducted where cases containing images outside of the usable brightness range were rejected. As illustrated in Tables 36 and 37 below, this constraint drastically limited the number of subjects in the test set while generally improving the sensitivity and specificity of neural network model 160, 860.

TABLE 36

Usable range [mean − 50, mean + 50] − 112 cases

| Cohort | Accuracy | Sensitivity | Specificity |
| --- | --- | --- | --- |
| Curebase (Positives) | 0.83 | 0.83 | NA |
| JHS (Positives + Negatives) | 0.89 | 0.88 | 0.9 |
| KEI (Ocular Negatives) | 0.95 | NA | 0.95 |
| Overall | 0.89 | 0.84 | 0.94 |

TABLE 37

Usable range [mean − 40, mean + 40] − 71 cases

| Cohort | Accuracy | Sensitivity | Specificity |
| --- | --- | --- | --- |
| Curebase (Positives) | 0.85 | 0.85 | N/A |
| JHS (Positives + Negatives) | 0.89 | 1.0 | 0.83 |
| KEI (Ocular Negatives) | 1.0 | N/A | 1.0 |
| Overall | 0.91 | 0.88 | 0.95 |

Given the results above, a constraint of brightness in the range of [−40, +40] leaves only 71 cases, which means that most of the cases in the test set were rejected. Therefore, it is not recommended.

In another experiment, the same brightness ranges were used, with another constraint to check how many images were within the brightness range. As Table 38 shows, several experiments were carried out where the minimum number of images that had to pass the brightness range check was set to be 8, 7, 6, and 5. This means, for example, in case of minimum images=5, at least 5 images in each case must pass the brightness range to keep them in the set.

TABLE 38

Results of experiments with different brightness ranges and minimum required images to pass the criteria
Test Set with 64 Cases
(Accuracy, Sensitivity, Specificity [num of cases])

| Brightness Range | Min Images = 8 | Min Images = 7 | Min Images = 6 | Min Images = 5 |
| --- | --- | --- | --- | --- |
| Mean +50 | 0.89, 0.84, 0.94 [112] | 0.89, 0.86, 0.93 [154] | 0.89, 0.85, 0.93 [179] | 0.89, 0.84, 0.93 [188] |
| Mean +40 | 0.91, 0.88, 0.95 [71] | 0.87, 0.84, 0.90 [112] | 0.87, 0.83, 0.90 [141] | 0.87, 0.83, 0.90 [162] |

These results indicate that filtering out images based on brightness values improves performance. However, this filtering process also removes a significant amount of test cases, which makes it difficult for the end-user.

Further testing of neural network model 160, 860 also revealed that light temperature was another key factor in classifying images as COVID-19 positive or negative. This can be viewed as taking images under a yellow, white, or blue light.

Figure 18A:
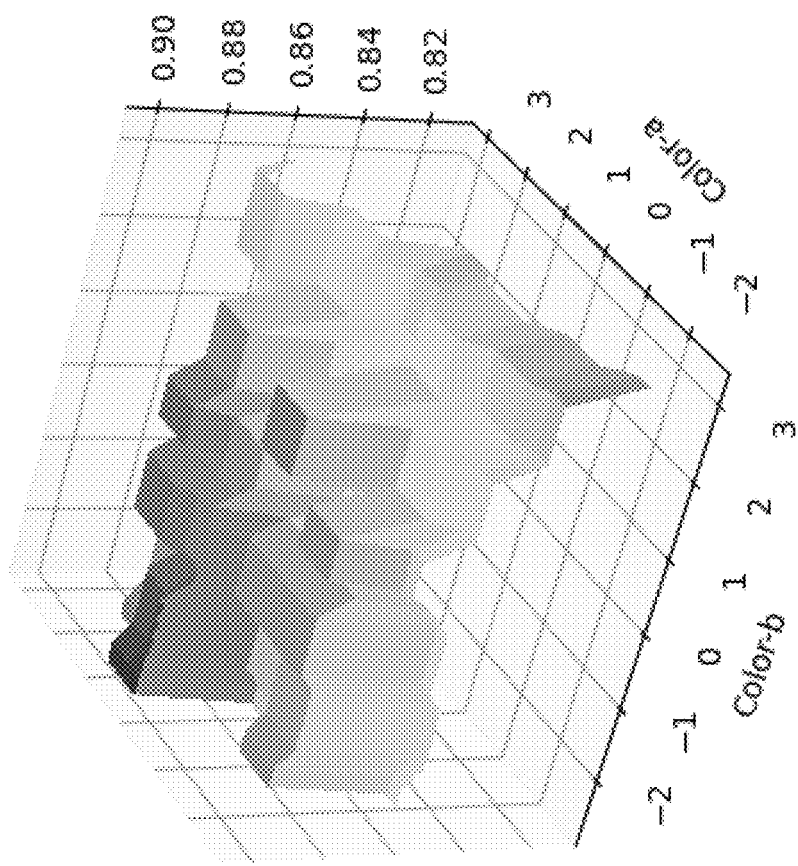
FIGS. 18A, 18B and 18C each depicts a model accuracy, sensitivity, and specificity changes, respectively, of neural network model performance against change of color in the input images.
Figure 18B:
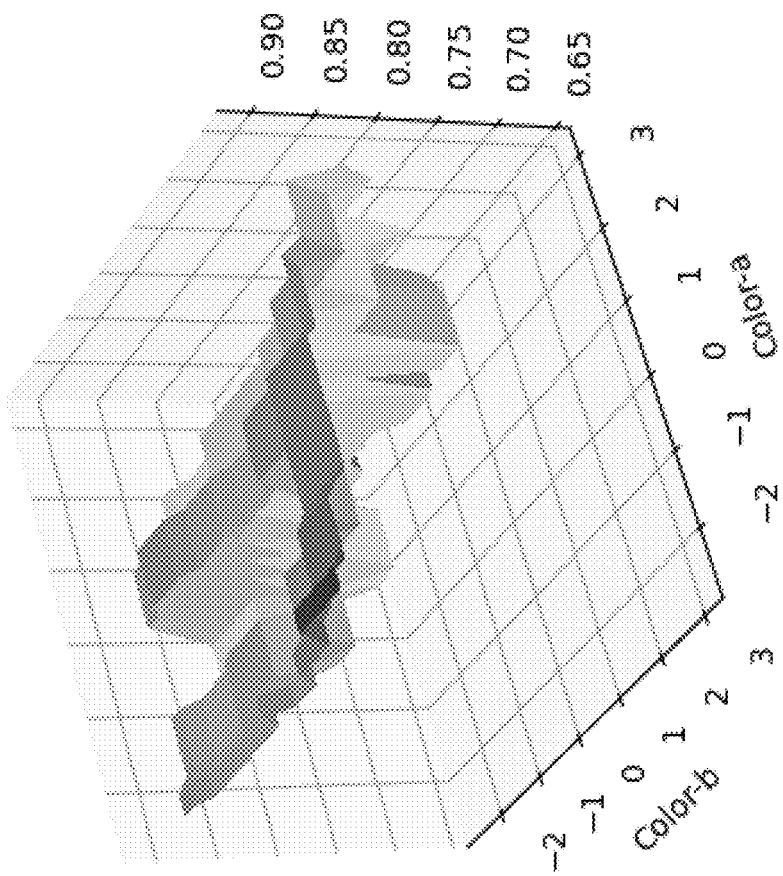
Figure 18C:
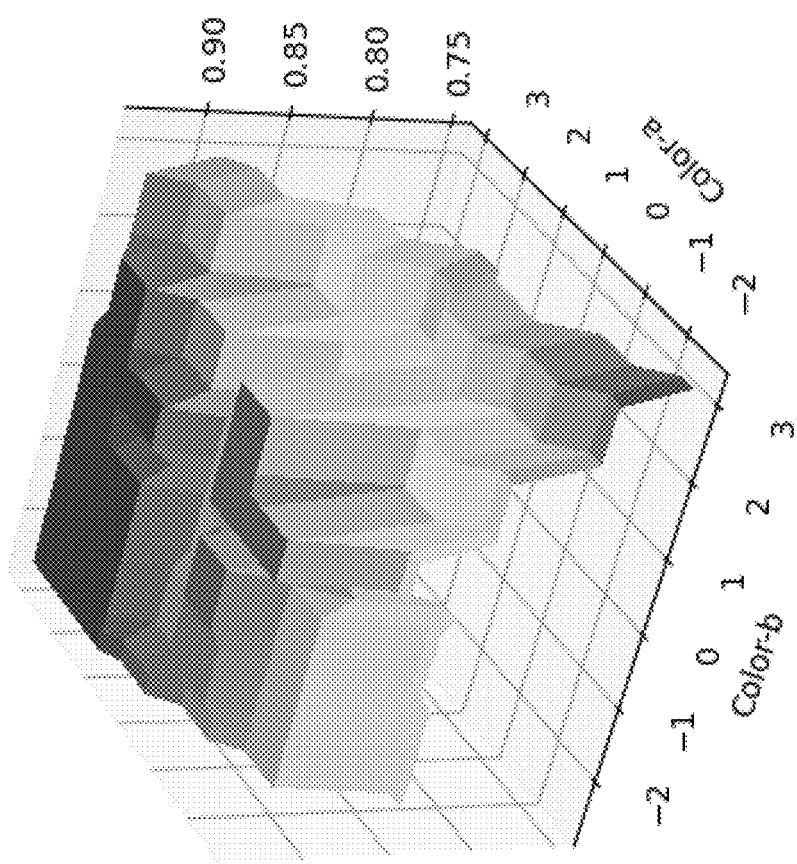

To study the effect of the color illumination on the model performance, the color of the test set images was adjusted or shifted, and then evaluated across various metrics. CIELab color space was used in this analysis. RGB images were converted to CIELab space using OpenCV. Both color-channels ("Lab-a" and "Lab-b") of the test set images were shifted in the range of [−2.3, 3.0] from the mean value of 129.1 and then evaluated. FIGS. 18A, 18B and 18C each depicts a model accuracy, sensitivity, and specificity changes of neural network model performance, respectively, against change of color in the input images.

Figure 19A:
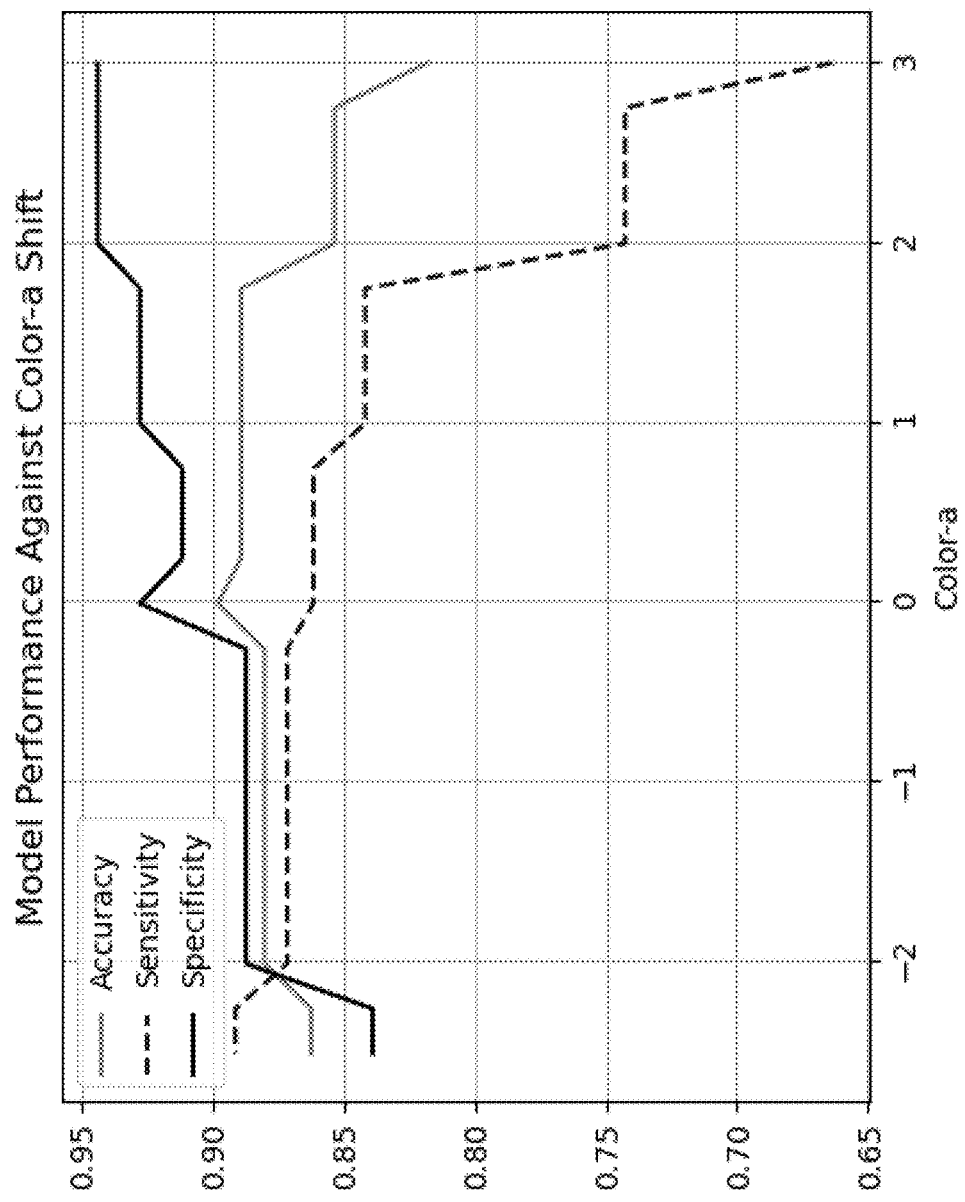
FIGS. 19A and 19B each shows plotted model performance metrics with change in a respective color channel (e.g., color-a or color-b) separately while keeping the other color channel constant.
Figure 19B:
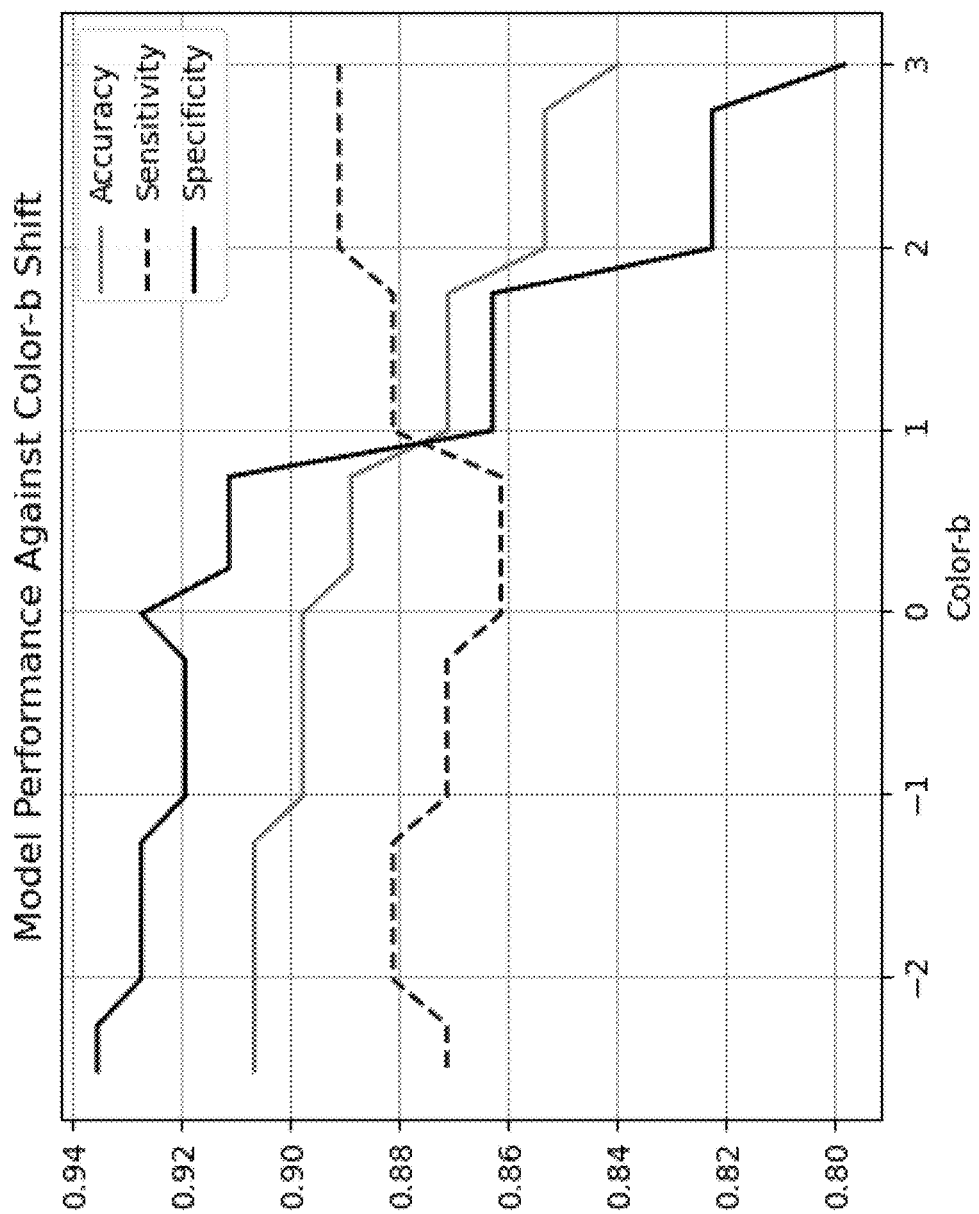

FIGS. 19A and 19B each shows plotted model performance metrics with change in a respective color channel (e.g., color-a or color-b) separately while keeping the other color channel constant.

Shifting towards the yellow side does not have much impact on the performance. However, shifting color to the blue side results in significant degradation to the specificity. Hence, there is more chance of False Positive (FP) cases in the blue side.

Here it can be observed that the color is a sensitive parameter for the model performance. There is a drop in specificity toward blue color in the sclera. Also, there is a drop in sensitivity towards red color in sclera. In other words, the trained neural network model generates more False Positives under blue light and more False Negatives under red light.

Post-Processing (Integrating Symptoms with Model Prediction)

To further boost the performance of the overall system, an ensemble system, such as shown in system 100, 100', is built to integrate symptoms identified in the test dataset together with neural network model 160, 860. In the following table, the eight top contributing symptoms and data points are shown.

TABLE 39

Symptoms that are collected during the data collection and labeled as important by a tree model

| Symptoms (Questionnaire) | Labels |
| --- | --- |
| Cough | Cough |
| Headache | Headache |
| Weakness or muscular pain | Muscle Pain |
| Sore throat or cold | Sore Throat |
| Gender | Gender |
| Recovered from COVID-19 in the last 30 days | Recovered |
| Received vaccination against COVID-19-19 infection | Vaccination |
| Ocular Surgery | Surgery |

Feature analysis on the training set was carried out to find the importance of these symptoms for prediction. The following figure and table show the results of the feature analysis.

TABLE 40

Symptoms ordered by their importance (weights) according to a regression model

| Symptoms | Weight (%) |
| --- | --- |
| Cough | 38.993 |
| Muscular Pain | 23.103 |
| Headache | 21.531 |
| Sore Throat | 8.724 |
| Recovered | 5.355 |
| Vaccination | 0.882 |
| Surgery | 0.773 |
| Gender | 0.639 |

Figure 20:
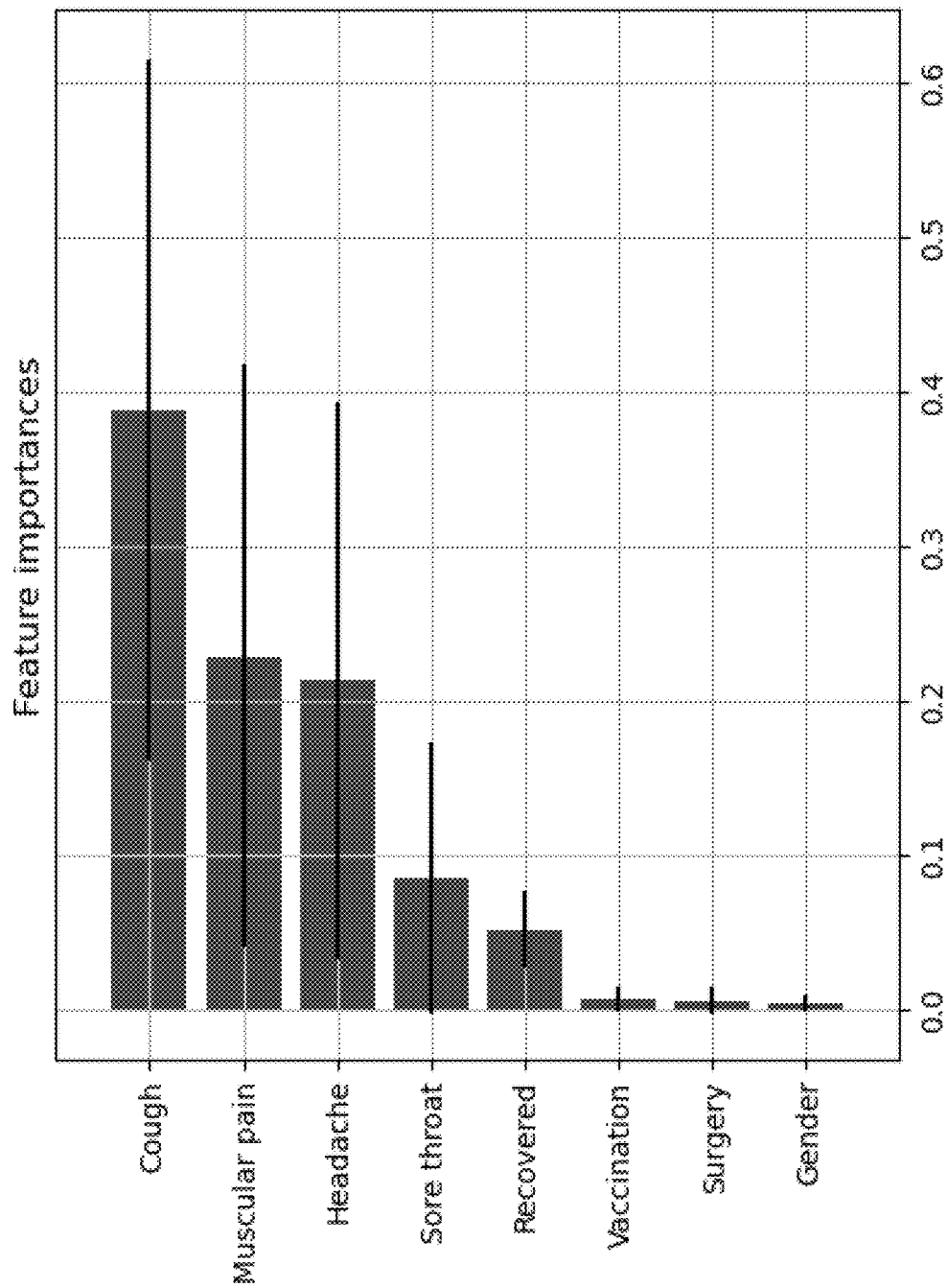
FIG. 20 shows a feature importance graph for the top four symptoms used as features to train a neural network model, in accordance with an embodiment.
Figure 21:
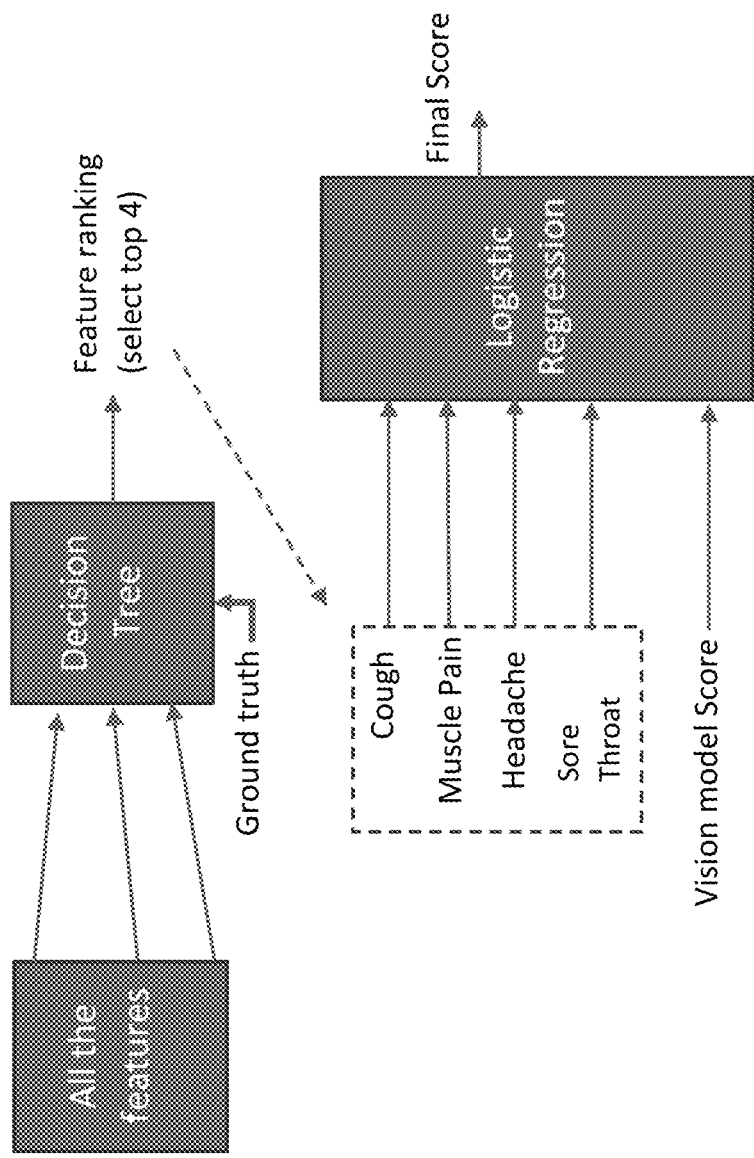
FIG. 21 shows a schematic block diagram illustrating the top four symptoms as feature selection and a corresponding final score of the neural network model, in accordance with an embodiment.

Based on the given weights above and feature importance graph in FIG. 20, it is clear that more than 92% of the weights are related to the first four symptoms (i.e., cough, muscular pain, headache, sore throat). Therefore, the top four symptoms are used for fine tuning of the neural network models 160, 860, which can be, for example, a logistic regression classifier. FIG. 21 shows a schematic block diagram illustrating the top four symptoms as feature selection and a corresponding final score of the neural network model, in accordance with an embodiment.

The example embodiments of system 100, 100', and in particular, of neural network model 160, 860 can predict the presence of COVID-19 manifestations above a confidence threshold. The system is also implemented to reject input images that are not of sufficient quality for the prediction process. A web application with a friendly user interface that is light and runnable on most smartphones has been built, with heavy computing processing delegated to the server side. The system is very robust due to at least the various pre-processing and checks in place to assess the quality of the input images.

As shown above, example embodiments of system 100, 100', and in particular, of neural network model 160, 860, perform well on the test datasets. Each test dataset used a different set of cameras to ensure that the datasets had different image qualities as well as various ISOs and Image Signal Processors (ISPs). This ensures model's capability in processing and predicting the presence of COVID-19 manifestations in patient's eyes regardless of patient's camera if it meets the minimum 5 mega-pixel requirement. The impact of varying camera specification on the performance of neural network model 160, 860 is reduced by combining low- and high-quality images.

According to the results discussed above, the impact of environment parameters like light intensity and temperature can be stronger than the smartphone camera specification. For instance, the brightness of input images may affect the performance of neural network model 160, 860. However, a shift of ±20 in the brightness level is found to be safe. Filtering out images based on brightness values improves performance. However, this filtering process removes a significant amount of test cases, which means user's input images can be rejected in runtime and can impact the quality of user experience significantly.

For another example, impact of color (light) temperature on the accuracy of the model is also observed. However, a small shift of ±2 in the color values was found to be safe. Generally, there is a drop in sensitivity towards the red color and drop in specificity towards the blue color.

Figure 13:
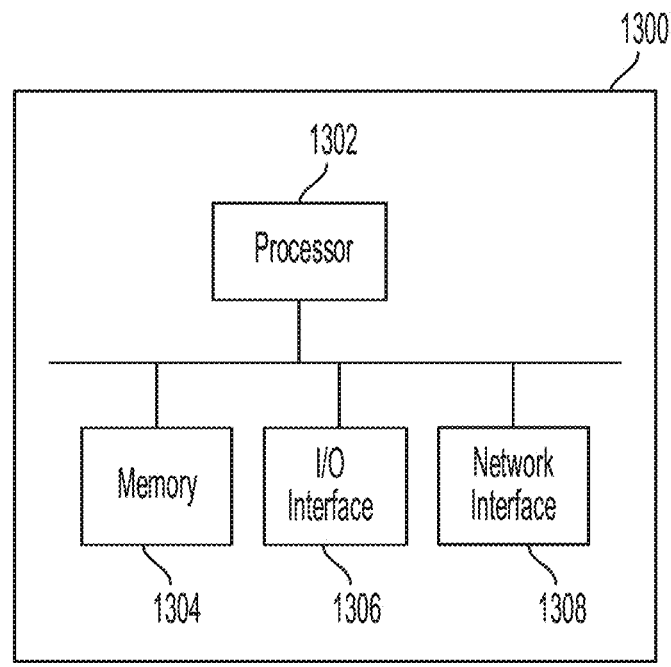
FIG. 13 is a schematic diagram for a computing device, in accordance with an embodiment.

FIG. 13 is a schematic diagram of computing device 1300 which may be used to implement assessment system 100, in accordance with an embodiment.

As depicted, computing device 1300 includes at least one processor 1302, memory 1304, at least one I/O interface 1306, and at least one network interface 1308.

Each processor 1302 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory 1304 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 1306 enables computing device 1300 to interconnect with one or more input devices, such as a keyboard, mouse, camera, touch screen and a microphone, or with one or more output devices such as a display screen and a speaker.

Each network interface 1308 enables computing device 1300 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

For simplicity only, one computing device 1300 is shown but system 100 may include multiple computing devices 1300. The computing devices 1300 may be the same or different types of devices. The computing devices 1300 may be connected in various ways including directly coupled, indirectly coupled via a network, and distributed over a wide geographic area and connected via a network (which may be referred to as "cloud computing").

For example, and without limitation, a computing device 1300 may be a server, network appliance, set-top box, embedded device, computer expansion module, personal computer, laptop, personal data assistant, cellular telephone, smartphone device, UMPC tablets, video display terminal, gaming console, or any other computing device capable of being configured to carry out the methods described herein.

In some embodiments, a computing device 1300 may be adapted to function as an end user device 200.

In some embodiments, a computing device 1300 may be adapted to implement assessment system 100'.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which may be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Of course, the above described embodiments are intended to be illustrative only and in no way limiting. The described embodiments are susceptible to many modifications of form, arrangement of parts, details and order of operation. The disclosure is intended to encompass all such modification within its scope, as defined by the claims.

The invention claimed is:

1. A computer-implemented method for predicting whether a user has a target health condition using eye images, the method comprising:
providing automated guidance to the user to obtain, using a computing device operated by the user, a plurality of images including the user's sclera, each of the images corresponding to a guided direction of the user's gaze;
receiving the images from the computing device by way of a network;
verifying that the images sufficiently show the user's sclera, including by estimating a direction of the user's gaze and confirming that the estimated direction for a given one of the images conforms with the guided direction corresponding to that image;
generating feature-enhanced image data by:
extracting an eye image of the user from at least one image from the plurality of images;
masking an iris area of the extracted eye image of the user in the at least one image such that the iris area of the extracted eye image is absent from downstream processing; and
applying an autoencoder to enhance features corresponding to the user's sclera in the at least one image to generate the feature-enhanced image data; and
computing a prediction of whether the user has the target health condition by providing the feature-enhanced image data to a convolutional neural network (CNN), wherein the feature-enhanced image data comprises image data representing ocular manifestations in the user's sclera and outside of the masked iris area in the extracted eye image in the at least one image, wherein the target health condition is related to coronavirus, and the CNN comprises a plurality of layers including a convolutional layer, an non-linear activation layer and a max-pooling layer.

2. The method of claim 1, wherein the automated guidance provides voice guidance to the user.

3. The method of claim 2, wherein the automated guidance provides the voice guidance in real time based on the direction of the user's gaze.

4. The method of claim 1, wherein the plurality of images include four images, each of the four images corresponding to the user's gaze being in a respective direction from up, down, left, and right directions.

5. The method of claim 1, wherein the ocular manifestations are associated with the target health condition.

6. The method of claim 1, wherein the convolutional neural network includes at least 16 layers.

7. The method of claim 1, further comprising:
transmitting to the computing device operated by the user an indication of whether the user has the target health condition based on the prediction.

8. The method of claim 1, wherein the at least one image from the plurality of images contains a face of the user, and generating the feature-enhanced image data of the at least one image comprises detecting the face of the user and extracting the eye image of the user from the detected face of the user.

9. The method of claim 8, wherein generating the feature-enhanced image data further comprises masking skin area outside of the extracted eye image in the detected face of the user in the at least one image.

10. A computer-implemented system for predicting whether a user has a target health condition using eye images, the system comprising:
at least one processor;
memory in communication with the at least one processor, and
software code stored in the memory, which when executed by the at least one processor causes the system to:
provide automated guidance to the user to obtain, using a computing device operated by the user, a plurality of images including the user's sclera, each of the images corresponding to a guided direction of the user's gaze;
receive the images from the computing device by way of a network;
verify that the images sufficiently show the user's sclera, including by estimating a direction of the user's gaze and confirming that the estimated direction for a given one of the images conforms with the guided direction corresponding to that image;
generate feature-enhanced image data by:
extracting an eye image of the user from at least one image from the plurality of images;
masking an iris area of the extracted eye image of the user in the at least one image such that the iris area of the extracted eye image is absent from downstream processing; and
applying an autoencoder to enhance features corresponding to the user's sclera in the at least one image to generate the feature-enhanced image data; and
compute a prediction of whether the user has the target health condition by providing the feature-enhanced image data to a convolutional neural network (CNN), wherein the feature-enhanced image data comprises image data representing ocular manifestations in the user's sclera and outside of the masked iris area in the extracted eye image in the at least one image, wherein the target health condition is related to coronavirus, and the CNN comprises a plurality of layers including a convolutional layer, an non-linear activation layer and a max-pooling layer.

11. The system of claim 10, wherein the automated guidance provides voice guidance to the user.

12. The system of claim 10, wherein the plurality of images include four images, each of the four images corresponding to the user's gaze being in a respective direction from up, down, left, and right directions.

13. The system of claim 10, wherein the ocular manifestations are associated with the target health condition.

14. The system of claim 10, wherein the convolutional neural network includes at least 16 layers.

15. The system of claim 10, wherein the software code stored in the memory, when executed by the at least one processor, further causes the system to:
transmit to the computing device operated by the user an indication of whether the user has the target health condition based on the prediction.

16. The system of claim 10, wherein the at least one image from the plurality of images contains a face of the user, and generating the feature-enhanced image data of the at least one image comprises detecting the face of the user and extracting the eye image of the user from the detected face of the user.

17. The system of claim 16, wherein generating the feature-enhanced image data further comprises masking skin area outside of the extracted eye image in the detected face of the user in the at least one image.

18. A non-transitory computer-readable medium having stored thereon machine interpretable instructions which, when executed by a processor, cause the processor to perform:
providing automated guidance to a user to obtain, using a computing device operated by the user, a plurality of images including the user's sclera, each of the images corresponding to a guided direction of the user's gaze;
receiving the images from the computing device by way of a network;
verifying that the images sufficiently show the user's sclera, including by estimating a direction of the user's gaze and confirming that the estimated direction for a given one of the images conforms with the guided direction corresponding to that image;
generating feature-enhanced image data by:
extracting an eye image of the user from at least one image from the plurality of images;
masking an iris area of the extracted eye image of the user in the at least one image such that the iris area of the extracted eye image is absent from downstream processing; and
applying an autoencoder to enhance features corresponding to the user's sclera in the at least one image to generate the feature-enhanced image data; and
computing a prediction of whether the user has the target health condition by providing the feature-enhanced image data to a convolutional neural network (CNN), wherein the feature-enhanced image data comprises image data representing ocular manifestations in the user's sclera and outside of the masked iris area in the extracted eye image in the at least one image, wherein the target health condition is related to coronavirus, and the CNN comprises a plurality of layers including a convolutional layer, an non-linear activation layer and a max-pooling layer.

* * * * *